United States Patent [19]

Johansson et al.

[11] Patent Number: 5,506,215
[45] Date of Patent: Apr. 9, 1996

[54] 1-(3'-FLUORO-2',3'-DIDEOXY-β-D-RIBOFURANOSYL)-5-SUBSTITUTED PYRIMIDINE NUCLEOSIDES

[75] Inventors: Karl N. G. Johansson, Enhörna; BjöG. Lindborg, Ävsjö ; Ulf Norinder; Goran B. Stening, both of Södertälje all of Sweden

[73] Assignee: Medivir AB, Huddinge, Sweden

[21] Appl. No.: 354,769

[22] Filed: Dec. 12, 1994

Related U.S. Application Data

[63] Continuation-in-part of Ser. No. 802,706, Dec. 6, 1991, abandoned, which is a continuation of Ser. No. 518,495, May 3, 1990, abandoned, which is a continuation-in-part of Ser. No. 266,402, Nov. 2, 1988, abandoned.

[30] Foreign Application Priority Data

Nov. 3, 1987 [SE] Sweden ................................. 8704298

[51] Int. Cl.$^6$ .................... A61K 31/70; C07H 19/073
[52] U.S. Cl. ................. 514/50; 514/49; 536/28.2
[58] Field of Search ................. 536/28.2; 514/49, 514/50

[56] References Cited

U.S. PATENT DOCUMENTS

| | | | |
|---|---|---|---|
| 3,282,921 | 11/1966 | Verheyden et al. | 536/28.2 |
| 3,687,931 | 8/1972 | Verheyden et al. | 536/27.14 |
| 3,775,397 | 11/1973 | Etzold et al. | 526/28.2 |
| 4,880,782 | 11/1989 | Eckstein et al. | 514/45 |
| 4,963,662 | 10/1990 | Matthes et al. | 514/45 |
| 5,008,252 | 4/1991 | Cheng et al. | 514/50 |
| 5,028,596 | 7/1991 | Purifoy et al. | 514/50 |

FOREIGN PATENT DOCUMENTS

| | | |
|---|---|---|
| 0066918 | 12/1982 | European Pat. Off. . |
| 0254268 | 1/1988 | European Pat. Off. . |
| 0317128 | 6/1989 | European Pat. Off. . |
| 0322384 | 6/1989 | European Pat. Off. . |
| 0356166 | 2/1990 | European Pat. Off. . |
| 0442757 | 8/1991 | European Pat. Off. . |
| 88/00050 | 1/1988 | WIPO . |

OTHER PUBLICATIONS

Remin et al. J. Amer Chem. Soc. 95(24):8146–8156, 1973.
Darzynkiewicz et al., Biochem. Biophys. Res. Commun. 46(4):1734–1741, 1972.
Darzynkiewicz et al. Biochem. Biophys. Res. Commun. 1:203–209, 1976.
Cusley et al. Cand. J. Chem. 46:1132–1140, 1968.
Kowollir et al. Journal f. prakt. Chemie, 315:895–900, 1973.
Herdewijn et al. J. Med. Chem. 30:1270–1278, 1987.

*Primary Examiner*—Gary L. Kunz
*Attorney, Agent, or Firm*—Birch, Stewart, Kolasch & Birch

[57] ABSTRACT

A 2',3'-deoxy-3'-fluoro-pyrimidine nucleoside having the formula:

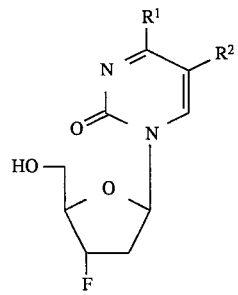

wherein
$R^1$ is OH or $NH_2$;
$R^2$ is $CF_3$, $CH_2CH_2CH_3$,

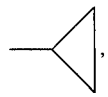

$CH_2OCH_3$, $CH_2SCH_3$, $CH=CH_2$ $CH=CH-CH_3$, $C\equiv CH$, $C\equiv C-CH_3$ or $CH_2-C\equiv CH$;
or a pharmaceutically acceptable salt thereof.

These nucleoside analogs exhibit antiviral activity against HIV.

6 Claims, No Drawings

1-(3'-FLUORO-2',3'-DIDEOXY-β-D-RIBOFURANOSYL)-5-SUBSTITUTED PYRIMIDINE NUCLEOSIDES

This application is a continuation of application Ser. No. 07/802,706 filed on Dec. 6, 1991, now abandoned; which is a continuation of application Ser. No. 07/518,495 filed on May 3, 1990, now abandoned; which is a continuation-in-part, of application Ser. No. 07/266,402 filed on Nov. 2, 1988, now abandoned.

FIELD OF THE INVENTION

The present invention relates to novel and known chemical compounds and pharmaceutically acceptable salts thereof for use in therapy for therapeutic and prophylactic control and treatment of the Acquired Immuno Deficiency Syndrome (AIDS), infections by Human Immunodeficiency Virus, hepatitis B virus infections and other retrovirus infections and method for such control and treatment in mammals and man.

BACKGROUND OF THE INVENTION

In the late seventies a new disease was reported, which subsequently was referred to as Acquired Immuno Deficiency, Syndrome (AIDS). It is now generally accepted that a retrovirus referred to as HIV (Human Immunodeficiency Virus), formerly known as Human T-cell Lymphotropic Virus (HTLV-III) or Lymphadenopathy Associated Virus (LAV) plays an essential role in the etiology of AIDS. Different types of HIV have been found, such as HIV-1 and HIV-2 and more are likely to be isolated.

AIDS is characterized by a profound immunodeficiency due to low numbers of a subset of lymphocyte-T-helper cells, which are one target for HIV infection. The profound immunodeficiency in AIDS patients makes these patients highly susceptible to a variety of opportunistic infections of bacterial, fungel, protozoal or vital etiology. The etiological agents among vital opportunistic infections are often found in the herpes virus group, i.e. Herpes simplex virus (HSV), Varicella Zoster virus (VZV), Epstein-Bart virus (EBV) and, especially, cytomegalovirus (CMV). Other retroviruses affecting humans are HTLV-I and II and examples of retroviruses affecting animals are feline leukemia virus and equine infectious anaemia virus. Human diseases such as multiple sclerosis, psoriasis and Kawasaki disease have also been reported to be associated with retrovirus infections.

Hepatitis B virus infections cause severe disease such as acute hepatitis, chronic hepatitis, fulminant hepatitis in a considerable number of persons. It is estimated that there are 200 million patients with chronic hepatitis B infection in the world. A considerable number of the chronic cases progress to liver cirrosis and liver tumours. In some cases the hepatitis infections also take a rapid and severe course as in fulminant B hepatitis with about 90% mortality. At present there is no known effective treatment against hepatitis B infections. The replication of hepatitis B virus is similar to that of retroviruses and it contains the same essential viral reverse transcriptase activity.

GENERAL OUTLINE OF THE INVENTION

A great number of nucleoside analogues exhibit several antimetabolic activities. They do so by substituting for or competing with the naturally occuring nucleosides. Recently some nucleoside analogues have been described, which inhibit in cell culture the multiplication of human immunodeficiency virus (HIV, also called HTLV-III, LAV), the causative agent of AIDS and AIDS-related complex (ARC).

We have now found that activities for inhibition of HIV multiplication are exhibited by nucleoside analogues, in which the nucleoside bases are both natural and modified and the sugar moieties have the 2'-deoxyribofuranosyl structure and the arabinofuranosyl structure with the 3'-substituent in both cases being an electronegative, non hydroxylic functionality.

PRIOR ART

Nucleoside analogues which have an inhibitory effect on the multiplication of HIV are described in EP-A2-199 451 and EP-A2-217 580, referring to 3'-azidonucleosides, such as azidothymidine, of the general formula

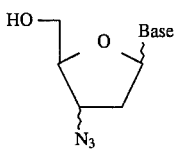

In EP-A2-206 497 2',3'-dideoxynucleosides are described to have good activity against different human viruses such as HTLV and hepatitis B virus. Said compounds are of the general formula

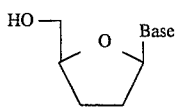

The following compounds are known:
1. The compound of the formula

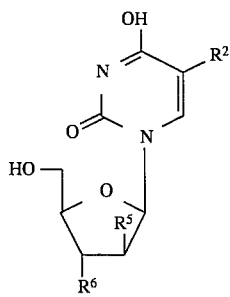

wherein
R$^2$=H, R$^5$=OH and R$^6$=F, Cl, is described by J. Cushley, J. F. Codington, J. J. Fox, Can. J. Chem. 46 (1968) 1131;

$R^2=C_2H_5$, $R^5=H$ and $R^6=F$ is described by P. Herdewijn et al, J. Med. Chem. 30 (1987) 1270–1278.

2. The compound of the formula

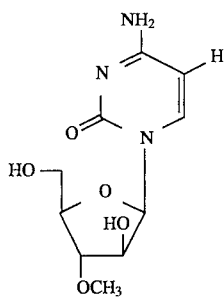

is described by E. Darzynkiewicz, J. T. Kuzmierek, D. Shugar, Biochem. Biophys. Res. Commun. 1972 46(4) 1734–41; and by M. Remin, D. Shugar, J. Am. Chem. Soc. 95 (1973) 8146.

3. The compound of the formula

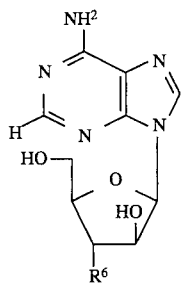

wherein $R^6=F$ is described by K. Miyai, R. K. Robins, R. L. Tolman, J. Med. Chem. 15 (1972) 1092;

$R^6=Cl, Br, I$ by R. Mengel, H. Wiedner, Chem. Ber 109 (1976) 1395;

$R^6=OCH_3$ by E. Darzynkiewicz, Z. Kazimierczuk, D. Shugar, Cancer, Biochem., Biophys. 1 (1976) 203.

DISCLOSURE OF THE INVENTION

It has been found according to the present invention that the compounds of the formula

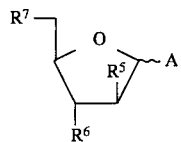

wherein A is

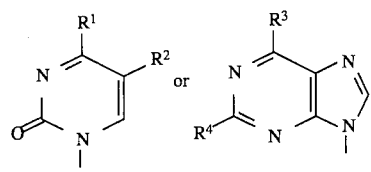

and the radicals $R^1$, $R^2$, $R^3$, $R^4$, $R^5$, $R^6$ and $R^7$ are defined as follows:

$R^1$: OH, $NH_2$;

$R^2$: H, F, Cl, Br, I, $CF_3$, $CH_3$, $CH_2CH_3$, $CH_2CH_2CH_3$,

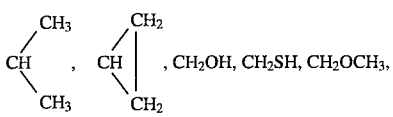

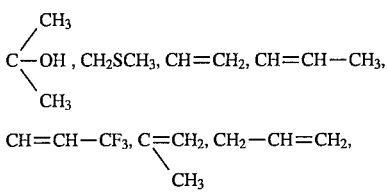

$CH=CH-CF_3$, $C=CH_2$, $CH_2-CH=CH_2$,
        $\quad\quad\quad\quad\quad\ \ \backslash CH_3$ $C\equiv CH$, $C\equiv C-CH_3$, $C\equiv C-CF_3$, $CH_2-C\equiv CH$;

$R^3$: H, OH, $NH_2$;
$R^4$: H, OH, $NH_2$;
$R^5$: H, OH, $OCH_3$;
$R^6$: H, F, Cl, Br, I, $OCH_3$, CN, $C\equiv CH$, $N_3$;
$R^7$: F, Cl, Br, I, OH or an ether or ester residue;

with the following provisos:

a) when $R^5=H$, then $R^6\neq H, N_3$;

b) when $R^5=H$, $R^7=OH$ and A=thymine, cytosine, β-adenine or β-guanine, then $R^6\neq F$;

c) when, in α-anomers, $R^5=H$, $R^7=OH$ and $R^1=OH, NH_2$, then

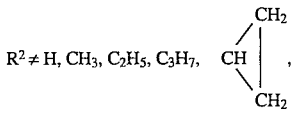

$CH=CH_2$, $CH=CH-CH_3$, $CH_2-CH=CH_2$, $C=CH_2$, $C\equiv CH$;
        $\quad\quad\quad\quad\ \ \backslash CH_3$ d) when $R^5=H$, $R^7=OH$, $R^1=OH$, $R^2=H$, $CH_2CH_3$, Br, $CH_2OH$ then $R^6\neq F$;

e) when $R^5=H$, $R^7=OH$, $R^1=NH_2$, $R^2=CH_3$ then $R^6\neq F$;

f) when $R^5=OH$, $R^7=OH$, $R^1=NH_2$, $R^2=H$ then $R^6\neq F$;

and pharmaceutically acceptable salts thereof, inhibit the multiplication of human immunodeficiency virus (HIV). The compounds of the formula I are useful as therapeutic and/or prophylactic agents in the control and treatment of HIV virus infections in mammals and man.

In a more general aspect, the compounds of the formula I are useful as therapeutic and/or prophylactic agents in the control and treatment of infections caused by retroviruses and hepatitis B virus in mammals and man.

All retroviruses, including HIV, require the enzyme reverse transcriptase in their natural cycle of replication.

Hepatitis B virus (HBV) is a DNA virus with a unique circular double-stranded DNA genome which is partly single-stranded. It contains a specific DNA polymerase required for vital replication. This DNA polymerase also acts as a reverse transcriptase during the replication of HBV DNA via an RNA intermediate.

The compounds of the formula I inhibit the activity of reverse transcriptase of retroviruses including HIV as well as the activity of DNA polymerase-reverse transcriptase of hepatitis B virus.

The present invention has several aspects:

1. a compound of the formula I for use in therapy, 2. use of a compound of the formula I in the manufacture of a medicament for therapeutic and/or prophylactic treatment of infections caused by a retrovirus, including HIV, or by hepatitis B virus, 3. a pharmaceutical composition comprising a compound of the formula I as active ingredient, 4. a method for the therapeutic and/or prophylactic treatment of infections in mammals and man caused by a retrovirus, including HIV, or a hepatitis B virus, by administering to a host in need of such treatment an efficient amount of a compound of the formula I, 5. the novel compounds included in the formula I.

It is a preferred aspect of the invention to combat HIV virus infections in man.

The invention comprises α-anomers as well as β-anomers of the compounds of formula I. In α-anomers $R^5$ and A are in trans-configuration and in β-anomers in cis-configuration.

Preferred compounds of the formula I are those wherein A is

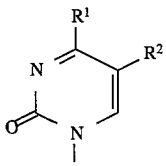

wherein $R^1$=OH, $NH_2$ and $R^2$=H, F, $CF_3$, $CH_3$, $C_2H_5$, CH=CH—$CH_3$,

$CH_2OH$, especially wherein $R^2$=H, $CH_3$, $C_2H_5$; or A is

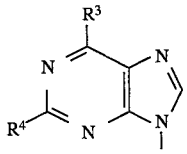

wherein $R^3$=H, OH, $NH_2$ and $R^4$=$NH_2$, H; and/or $R^6$=F, $N_3$, CN, $OCH_3$, C≡CH and $R^7$=OH or an ester residue.

Examples of preferred compounds are those of the formula

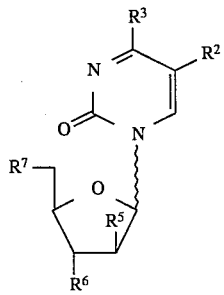

wherein $R^1$=OH, $R^2$=$CH_3$, $R^5$=OH, $R^6$=F, $R^7$=OH;
$R^1$=OH, $R^2$=$CH_3$, $R^5$=OH, $R^6$=$N_3$, $R^7$=OH;
$R^1$=OH, $R^2$=$CH_3$, $R^5$=OH, $R^6$=CN, $R^7$=OH;
$R^1$=OH, $R^2$=$CH_3$, $R^5$=OH, $R^6$=$OCH_3$, $R^7$=OH;

$R^1$=OH, $R^2$=$C_2H_5$, $R^5$=OH, $R^6$=F, $R^7$=OH;
$R^1$=OH, $R^2$=$C_2H_5$, $R^5$=OH, $R^6$=$N_3$, $R^7$=OH;
$R^1$=OH, $R^2$=$C_2H_5$, $R^5$=OH, $R^6$=CN, $R^7$=OH;
$R^1$=OH, $R^2$=$C_2H_5$, $R^5$=OH, $R^6$=$OCH_3$, $R^7$=OH;
$R^1$=OH, $R^2$=$C_2H_5$, $R^5$=H, $R^6$=F, $R^7$=OH;
$R^1$=OH, $R^2$=$C_2H_5$, $R^5$=H, $R^6$=F, $R^7$=$OCOCH_3$;
$R^1$=OH, $R^2$=CH=CH—$CH_3$, $R^5$=OH, $R^6$=F, $R^7$=OH;
$R^1$=OH, $R^2$=CH=CH—$CH_3$, $R^5$=OH, $R^6$=$N_3$, $R^7$=OH;
$R^1$=OH, $R^2$=CH=CH—$CH_3$, $R^5$=OH, $R^6$=CN, $R^7$=OH;
$R^1$=OH, $R^2$=CH=CH—$CH_3$, $R^5$=OH, $R^6$=$OCH_3$, $R^7$=OH;
$R^1$=$NH_2$, $R^2$=$CH_3$, $R^5$=H, $R^6$=F, $R^7$=OH;
$R^1$=$NH_2$, $R^2$=$C_2H_5$, $R^5$=H, $R^6$=F, $R^7$=OH;
$R^1$=$NH_2$, $R^2$=H, $R^5$=OH, $R^6$=F, $R^7$=OH;
$R^1$=$NH_2$, $R^2$=H, $R^5$=OH, $R^6$=$N_3$, $R^7$=OH;
$R^1$=$NH_2$, $R^2$=H, $R^5$=OH, $R^6$=CN, $R^7$=OH;
$R^1$=$NH_2$, $R^2$=H, $R^5$=OH, $R^6$=$OCH_3$, $R^7$=OH;
$R^1$=$NH_2$, $R^2$=CH=CH—$CH_3$, $R^5$=OH, $R^6$=F, $R^7$=OH;
$R^1$=$NH_2$, $R^2$=CH=CH—$CH_3$, $R^5$=OH, $R^6$=$N_3$, $R^7$=OH;
$R^1$=$NH_2$, $R^2$=CH=CH—$CH_3$, $R^5$=OH, $R^6$=CN, $R^7$=OH;
$R^1$=$NH_2$, $R^2$=CH=CH—$CH_3$, $R^5$=OH, $R^6$=$OCH_3$, $R^7$=OH;

and of the formula

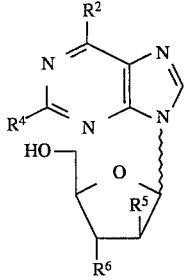

$R^3$=H, $R^4$=$NH_2$, $R^5$=H, $R^6$=F;
$R^3$=H, $R^4$=$NH_2$, $R^5$=OH, $R^6$=F;
$R^3$=OH, $R^4$=$NH_2$, $R^5$=OH, $R^6$=F;
$R^3$=OH, $R^4$=$NH_2$, $R^5$=OH, $R^6$=$N_3$;
$R^3$=OH, $R^4$=$NH_2$, $R^5$=OH, $R^6$=CN;
$R^3$=OH, $R^4$=$NH_2$, $R^5$=OH, $R^6$=$OCH_3$;
$R^3$=$NH_2$, $R^4$=H, $R^5$=OH, $R^6$=F;
$R^3$=$NH_2$, $R^4$=H, $R^5$=OH, $R^6$=$N_3$;
$R^3$=$NH_2$, $R^4$=H, $R^5$=OH, $R^6$=CN;
$R^3$=$NH_2$, $R^4$=H, $R^5$=OH, $R^6$=$OCH_3$;
$R^3$=OH, $R^4$=H, $R^5$=H, $R^6$=F;
$R^3$=OH, $R^4$=H, $R^5$=OH, $R^6$=F;

Esters and ethers of the nucleosides are also included in the invention. Examples of esters are phosphate esters, carboxylic esters, carbonate esters or sulphonic esters. The acid part of the esters may have alkyl, aryl or arylalkyl chains, where the aryl functionalities are optionally substituted for example by alkoxy, amino, nitrile, alkyl or sulphonamido groups or by one or more halogen atoms. Examples of other types of derivatives of the nucleosides are alkyl or arylalkyl derivatives of the 5' hydroxyl group. The arylalkyl ether derivatives may be for example benzyl or triphenyl methyl and the aryl moiety may be optionally substituted. Furthermore, it is understood that the examples of the pharmaceutically acceptable salts cited below also apply to the various esters or derivatives of the nucleosides of the invention.

In a compound of the formula I $R^7$ as an ether residue can be defined as $OR^8$, wherein $R^8$ is $C_{1-6}$ alkyl arylalkyl optionally substituted with one or more alkoxy, amino, nitrile or sulphonamido groups or one or more halogen atoms.

$R^7$ as an ester residue can be derived from a carboxylic acid $R^9COOH$, a carbonic acid $R^{10}.O.COOH$, a sulphonic acid $R^{10}SO_2.OH$ or a phosphoric acid, wherein $R^9$ is H, $C_{1-17}$ alkyl, preferably $C_{1-6}$ alkyl, arylalkyl or aryl and $R^{10}$ is $C_{1-17}$ alkyl, preferably $C_{1-6}$ alkyl, arylalkyl or aryl, and said aryl and arylalkyl groups optionally can be substituted with one or more alkyl, alkoxy, amino, nitrile, sulphonamido groups or one or more halogen atoms.

Examples of pharmaceutically acceptable salts of the compounds of formula I include base salts, e.g. derived from an appropriate base, such as alkali metal (e.g. sodium), alkaline earth metal (e.g. magnesium) salts, ammonium and $NX_4^+$ (wherein X is $C_{1-4}$ alkyl). Physiologically acceptable salts of a hydrogen atom or an amino group include salts of organic carboxylic acids such as acetic, lactic, gluconic, citric, tartaric, maleic, malic, pantothenic, isethionic, succinic, oxalic, lactobionic and succinic acids; organic sulfonic acids such as methanesulfonic, ethanesulfonic, benzenesulfonic, p-chlorobenzenesulphonic and p-toluenesulfonic acids and inorganic acids such as hydrochloric, hydroiodic, sulfuric, phosphoric and sulfamic acids. Physiologically acceptable salts of a compound of an hydroxy group include the anion of said compound in combination with a suitable cation such as $Na^+$, $NH_4^+$, and $NX_4^+$ (wherein X is a $C_{1-4}$ alkyl group).

In clinical practice the nucleosides of the formula I will normally be administered orally, by injection or by infusion in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material. As examples of pharmaceutical preparations may be mentioned tablets, dragees, capsules, granulates, suspensions, elixirs, syrups, solutions, liposomes etc. Usually the active substance will comprise between 0.05 and 20% for preparations intended for injection and between 10 and 90% for preparations intended for oral administration.

In the treatment of patients suffering from retrovirus, especially HIV, or hepatitis B virus infections, it will be preferred to administer the compounds by any suitable route including the oral, parenteral, rectal, nasal, topical and vaginal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of patient etc., and may have to be individually adjusted. As a possible range for the amount of the compounds of the invention or a physiologically acceptable salt thereof to be administered per day may be mentioned from about 10 mg to about 10 000 mg, preferentially 100–500 mg for intravenous administration and preferentially 100–3000 mg for oral administration.

Those compounds of the formula I which are novel are those of the formula I with the provisos that a) when $R^5$=H, then $R^6 \neq H$, $N_3$;

b) when $R^5$=H, $R^7$=OH and A=thymine, cytosine, β-adenine or β-guanine, then $R^6 \neq F$;

c) when, in α-anomers, $R^5$=H, $R^7$=OH and $R^1$=OH, $NH_2$, then

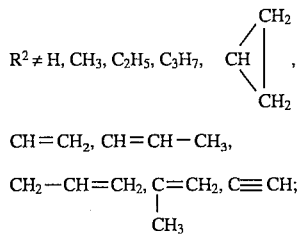

$CH=CH_2$, $CH=CH-CH_3$, $CH_2-CH=CH_2$, $\underset{CH_3}{C}=CH_2$, $C\equiv CH$;

d) when $R^5$=H, $R^7$=OH, $R^1$=OH, $R^2$=H, $CH_2CH_3$, Br, $CH_2OH$ then $R^6 \neq F$;

e) when $R^5$=H, $R^7$=OH, $R^1$=$NH_2$, $R^2$=$CH_3$ then $R^6 \neq F$;

f) when $R^5$=OH, $R^7$=OH, $R^1$=$NH_2$, $R^2$=H then $R^6 \neq F$;

g) when $R^5$=H, $R^7$=F, J, $R^1$=OH, $R^2$=$CH_3$, then $R^6 \neq F$;

h) when $R^5$=H, $R^7$=$OCOR^9$, $OSO_2R^{10}$, $R^9$=$CH_3$, $R^{10}$=$CH_3$, $R^1$=OH, $R^2$=$CH_3$ then $R^6 \neq F$;

i) when $R^5$=H, $R^7$=OH, $R^1$=OH, $R^2$=F, $CF_3$, then $R^6 \neq OCH_3$;

k) when $R^5$=H, $R^7$=OH, $R^1$=OH, $NH_2$, $R^2$=H, F, Cl, Br, J, $CH_3$ then $R^6 \neq F$;

l) when $R^5$=H, $R^7$=F, Cl, Br, J, $R^1$=OH, $NH_2$, $R^2$=H, F, Cl, Br, J, $CF_3$ then $R^6 \neq H$, F, Cl, Br, J;

m) when $R^5$=H, $R^7$=$OCOR^9$, $R^9$=$CH_3$, $R^1$=OH, $R^2$=$CH_3$ then $R^6 \neq J$;

n) when $R^5$=H, $R^7$=OH, $R^1$=OH, $R^2$=$CH_2CH_3$ then $R^6 \neq Cl$;

o) when $R^5$=H, $R^7$=OH, $R^3$=$NH_2$, $R^4$=$NH_2$, OH then $R^6 \neq OCH_3$;

p) when $R^5$=OH, $R^7$=OH, $R^1$=OH, $R^2$=H then $R^6 \neq C\equiv CH$, CN q) when $R^5$=OH, $R^7$=OH, $R^1$=OH, $R^2$=H, then $R^6 \neq F$; Cl, J;

r) when $R^5$=OH, $R^7$=OH, $R^1$=$NH_2$, $R^2$=H, then $R^6 \neq OCH_3$;

s) when $R^5$=OH, $R^7$=OH, $R_3$=$NH_2$, $R^4$=H, then $R^6 \neq F$, Cl, Br, I, $OCH_3$.

Compounds of the formula I cooperate synergistically or additively with a wide range of other therapeutic agents, thereby enhancing the therapeutic potential of both agents without adding the toxic effects, thus increasing the therapeutic ratio.

Therefore, a compound of formula I or a pharmaceutically acceptable derivative thereof can be used in combination therapy, wherein the two active agents are present in a ratio resulting in an optimal therapeutic ratio. This can be provided either by a synergistic effect against the viral infection and/or by a decrease in toxicity while maintaining a therapeutic effect which is additive or synergistic. A combination therapy can also be of use to obtain effects on different types of cells infected with HIV and requiring different drugs for effect.

The optimal therapeutic ratio is observed when the two agents are present in a ratio of 500:1 to 1:500, preferably 100:1 to 1:100, particularly 20:1 to 1:20 and especially 10:1 to 1:10.

Said combinations may conveniently be administered together, for example, in a unitary pharmaceutical formulation, or separately, for example as a combination of tablets and infections administered at the same time or different times, in order to achieve the required therapeutic effect.

The compounds of the formula I are potentiated by interferons, reverse transcriptase inhibitors, such as foscarnet, AZT, glucuronidation inhibitors, renal excretion inhibitors, HIV protease inhibitors, immunomodulators, interraton inducers and growth factors.

Particularly preferred types of interferon are α, β and γ and interferon inducers such as "Ampligen" (Hem Research).

Probenecid is particularly useful in combination with compounds of the formula I, as it possesses both renal excretion inhibiting activity and glucuronidation blocking activity. Examples of other compounds useful in this aspect include acetaminophen, aspirin, lorazepam, cimetidine, ranitidine, zomepirac, clofibrate, indomethacin, ketoprofen, naproxen and other compounds which compete for glucuronidation or otherwise undergo significant glucuronidation.

Other combinations suitable for use according to the present invention include those wherein the second agent is, for example, interleukin II, suramin, foscarnet or an ester thereof, HPA 23, inhibitors of HIV protease such as pepstatin, steroids, medications such as levamisol or thymosin to increase lymphocyte numbers and/or function as appropriate, or GM-CSF and other factors regulating cell functions.

Methods of Preparation

The compounds of the invention may be prepared by one of the following general methods, constituting a further aspect of the invention.

A. Condensing a glycoside as comprised in formula I where the hydroxyl groups may be optionally protected, to the N-1 position of a pyrimidine derivative or to the N-9 position of a purine derivative, according to known methods described in the literature. Such methods are described for example in "Basic Principles in Nucleic Acid Chemistry", Vol. 1 (Academic Press, 1974, Ed. P.O.P.Ts'o), in "Nucleoside Analogues, Chemistry, Biology and Medical Applications" (Pharma Press, 1979, Eds. R. T. Walker, E. De Clercq and F. Eckstein).

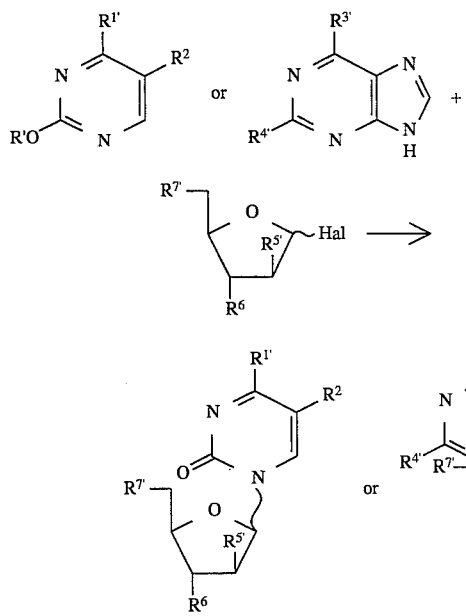

Examples of suitable derivatives of the reacting species are those wherein R' is $C_2H_5$ or $(CH_3)_3Si$; $R^{1'}$ is $OC_2H_5$, $(CH_3)_3SiO$, or $N(COCH_3)Si(CH_3)_3$; $R^{3'}$ is Cl, O-alkyl, NH-acyl or NH-benzoyl; $R^{4'}$ is $R^4$ as defined above, NH-acyl or NH-benzoyl; $R^{5'}$ is H, $OCH_3$, O-acyl, O-benzoyl, O-benzyl or O-silyl (e.g. dimethyl, tert-butylsilyl); $R^{7'}$ is halogen or $OR^8$ wherein $R^8$ is as defined above or silyl (e.g. dimethyl, tert-butylsilyl), except that now it must not be H; $R^2$ and $R^6$ are as defined above.

After condensation the products may be hydrolyzed or converted by conventional methods, known to those skilled in the art, into compounds of the formula I.

The glycosides are known or may be prepared by suitable adaptions of known methods. The synthesis of a 2,3-dideoxy-3-fluoro-erythro-pentofuranoside for example, has been described by G. W. J. Fleet and J. C. Son in Tetrahadron Letters 40 (1987) pp 3615–3618. The other $R^6$ substituents may be introduced by methods analogous to those described above and described by N. B. Dyathina and A. V. Azhayev in Synthesis, 1984, pp 961–963. The arabinosylglycosides may be prepared by similar methods.

B. The β-anomers of the arabinosyl-pyrimidine nucleoside analogues may be prepared by hydrolysis of the corresponding 2,2'-anhydro nucleoside analogues.

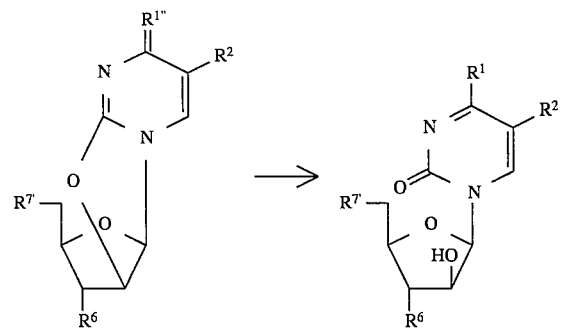

wherein $R^{1'''}$ is O or NH and $R^1$, $R^2$, $R^6$ and $R^{7'}$ are as defined above. The hydrolysis may be performed by conventional methods, described in the literature and known to those skilled in the art. It may for example be performed by treating the 2,2'-anhydronucleosides with an aqueous acid.

C. The halogeno, $OCH_3$, $N_3$, CN and C≡CH substituents in the 3' position of the glycon moiety may be introduced by substitution of a hydroxyl group or a suitably derivatized hydroxyl group

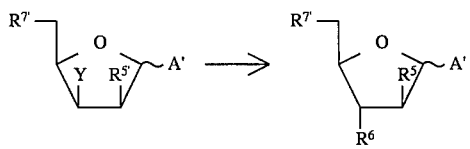

wherein A' is

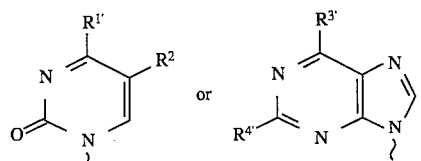

Y is OH or a functionality that will be leaving in the substitution reaction such as for example $CF_3SO_3$; and $R^{1'}$, $R^2$, $R^{3'}$, $R^{4'}$, $R^{5'}$, $R^6$ and $R^{7'}$ are as defined above D. The 3'-substituted arabinosyl nucleosides may be prepared by ring opening of the corresponding 1-(2',3'-anhydro-D-lyxofuranosyl)nucleosides.

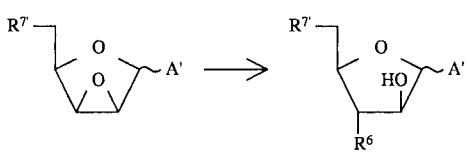

wherein A' is

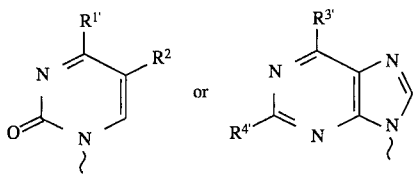

$R^{1'}$, $R^2$, $R^{3'}$, $R^{4'}$, $R^{5'}$, $R^6$ and $R^{7'}$ are as defined above.

The epoxide opening may be performed by conventional methods described in the literature and known to those skilled in the art.

The epoxide compound may be prepared from condensation of the nucleobase or nucleobase analogue with 1-O-acetyl-D-ribofuranose or -xylofuranose with protecting groups on the oxygen atoms, followed by transformation of the ribofuranosyl or the xylofuranosyl ring into a 2',3'-anhydro-lyxofuranosyl moiety by known methods.

The following examples will further illustrate the invention.

EXAMPLE I

Preparation of 1-(3'-F-2',3'-dideoxy-β-D-ribofuranosyl)-uracil (VSA-417)

Uracil (42.5 mg) and 3'-F-3'-deoxythymidine was suspended in acetonitril (1.2 ml) and N,O-bis(trimethylsilyl)acetamide (0.35 ml) was added. The mixture was stirred at room temperature for 1.5 h. Trimethylsilyl trifluoromethanesulfonate (0.05 ml) was added. After stirring at room temperature for 188 h the mixture was evaporated in vacuum and added to $H_2O$ (0.5 ml), filtered and washed with $H_2O$ (0.5 ml). The combined water phase was applied to $C_{18}$-column (HPLC) and eluated with methanol-water (1:9) at a rate of 9.5 ml/min. The desired β-anomer, VSA-417, eluated after 9.75 min, and the α-anomer VSA-418 after 8.0 min.

Yield 1.8 mg (3%).

$^1$H-NMR (DMSO-$d_6$) δ: 4.26 (dt, 1H, J3'F,4'=29.4 Hz, J4'5'=1.5 Hz, H-4'), 5.40 (dd, 1H, J3'F,3'=53.7 Hz, J2',3'=4.9 Hz, H-3'), 5.66 (d, 1H, J5,6=8.3 Hz, H-5), 6.31 (dd, 1H, J=5.7, J=8.8 Hz, H-1'), 7.81 (d, 1H, J5,6=8.3 Hz, H-6).

EXAMPLE II

Preparation of 1-(3'-F-2',3'-dideoxy-β-D-ribofuranosyl)-5-ethyl-uracil (VSA-410)

5-Ethyluracil (51 mg) and 3'-F-3'-deoxythymidine (48 mg) was suspended in acetonitrile (1.2 ml) and N,O-bis(trimethylsilyl)acetamide (0.35 ml) was added. The mixture was stirred at room temperature for 1.5 h. Trimethylsilyl trifluoromethane sulfonate (0.05 ml) was added. After stirring at room temperature for 161 h, the mixture was evaporated in vacuum, and added to water (0.5 ml), filtered and washed with water (0.5 ml). The combined water phase was applied to $C_{18}$-column (HPLC) and eluated with methanol-water (1:3) at a rate of 8.0 ml/min. The desired β-anomer, VSA-410, eluted after 12.3 min and the α-anomer, VSA 411, after 16.4 min. Yield 7.3 mg (14%). UV λ max ($H_2O$): 266 nm. MS M$^+$ 258 (7%), 140 (100%), 119 (64%).

EXAMPLE III

Preparation of 1-(3'-F-2',3'-dideoxy-β-ribofuranosyl)-5-propyl-uracil (VSA-408)

5-Propyluracil (56 mg) and 3'-F-3'-deoxythymidin (47 mg) was suspended in acetonitrile (1.2 ml) and N,O-bis(trimethylsilyl)acetamide (0.35 ml) was added. The mixture was stirred at room temperature for 1.5 h. Trimethylsilyl trifluoromethane sulfonate (0.05 ml) was added. After stirring at room temperature for 138 h, the mixture was evaporated in vacuum and added to $H_2O$ (0.5 ml), filtered and washed with $H_2O$ (0.5 ml). The combined water phase was applied to $C_{18}$-column (HPLC) and eluated with methanol-water (35:55), at a rate of 7.0 ml/min. The desired β-anomer, VSA 408, eluted after 12.9 min, and the α-anomer, VSA 409, after 18.0 min. Yield 3.6 mg (7%). UV λ max ($H_2O$): 267 nm. MS M$^+$ 272 (5%), 154 (100%), 119 (76%).

EXAMPLE IV

Preparation of 1-(2',3'-anhydro-5'-O-trityl-β-D-lyxofuranosyl)thymine (VSB-020)

The title compound was prepared by a 5-step sequence reaction. Thymine (12,6 g) was treated with hexamethyldisilazane and 1-O-acetyl-2,3,5-tri-O-benzoyl-β-D-ribofuranose (50 g) was added. The 1-(2',3',5'-tri-O-benzoyl-β-D-ribofuranosyl)thymine obtained was treated with sodium methoxide and gave 1-(β-D-ribofuranosyl)thymine (23 g). Then said substance was treated with tritylchloride and methylsulfonylchloride and 1-(2',3' -di-O-methylsulfonyl-5'-O-trityl-β-D-ribofuranosyl)thymine (39 g) was obtained. Said substance was treated with sodium hydroxide and gave the title compound 1-(2'-3'-anhydro-5'-O-trityl-β -D-lyxofuranosyl)thymine (VSB-020) 19.2 g. Yield 43%. $^1$H-NMR (DMSO-$d_6$) δ: 1.66 (s, 3H, 5-$CH_3$), 3.24–3.34 (m, 2H, 5'-H), 4.08 (s, 2H, 2'-H and 3'-H), 4.25 (t, 1H, 4'-H), 6.13 (s, 1H, 1'-H), 7.30–7.45 (m, 16H, trityl H and 6-H), 14.46 (s, 1H, N—H).

EXAMPLE V

Preparation of 1-(3'-deoxy-3'-ethynyl-β-D-arabinofuranosyl)thymine (VSB-029)

a) A suspension of an ethylene diamine complex of ethynyl lithium (275 mg, 3 mmol) in dry DMSO (5 ml) was stirred under nitrogen for 1 h at 20° C. A solution of 1-(2',3'-anhydro-5'-O-trityl-β -D-lyxofuranosyl)thymine (VSB-020; 482 mg) in dimethylsulfoxide (DMSO; 2 ml) was added with a syringe to the reaction suspension. The reaction mixture was kept at 20° C. for 48 h. The reaction mixture was then poured into a saturated ammonium chloride solution (100 ml) and extraced with ethyl acetate (2×100 ml). The organic phase was washed with a saturated ammonium chloride solution (100 ml), brine (100 ml) and water (100 ml) and dried over disodium sulfate. The solvent was evaporated and the residue purified on a silica gel column using toluene:ethyl acetate (7:4 v/v) as eluent. The appropriate fractions were collected and evaporation of the solvent gave 300 mg of 1-(3'-deoxy- 3'-ethynyl-5'-O-trityl-β-D-arabinofuranosyl)thymine (VSB-028). Yield 59%. $R_f$ 0.45 (silica, ethyl acetate).

b) A solution of 1-(3'-deoxy-3'-ethynyl-5'-O-trityl-β-D-arabinofuranosyl)thymine (VSB-028; 280 mg) in acetic acid (8 ml) and water (2 ml) was heated at 80° C. for 15 min. Then, the solvent was evaporated and the residue purified on a silica gel column, using first chloroform as the eluent followed by chloroform:ethanol (9:1 v/v). The combined fractions were evaporated and the residue was triturated with hexane:ethanol (9:1 v/v) to give 110 mg of the title compound (VSB-029). Yield 75%. M.p. 198°–199° C.

$^1$H-NMR (DMSO-$d_6$) δ: 1.75 (s, 3H, 5-CH$_3$), 2.89 (t, 1H, 3'-H), 3.18 (d, 1H, —C≡C—H), 3.55–3.79 (m, 3H, 4'-H and 5'-H), 4.41 (q (t on D$_2$O shake), 1H, 2'-H), 5.29 (t, 1H, 5'-OH), 5.97 (d, 1H, 2'-OH), 6.03 (d, J=6.22 Hz, 1H, 1'-H), 7.65 (s, 1H, 6-H), 11.25 (s, 1H, N—H).

EXAMPLE VI

Preparation of 1-(3'-cyano-3'deoxy-β-D-arabinofuranosyl)-thymine (VSB-026)

a) To a solution of VSB-020, 1-(2',3'-anhydro-5'-O-trityl-β -D-lyxofuranosyl)thymine (480 mg) in dry dimethylsulfoxide (DM SO) (10 ml) was added sodium cyanide (245 mg). The reaction mixture was heated at +45° C. for 15 h, whereafter a saturated ammonium chloride solution (50 ml) was added to the reaction mixture. The mixture was extracted with ethyl acetate (3×50 ml) and the combined organic layers were washed with a saturated ammonium chloride solution (50 ml); brine (50 ml) and H$_2$O (50 ml), dried over disodium sulfate and purified on a silica gel column using toluene:ethyl acetate (7:4 v/v) as eluent to give 160 mg of 1-(3'-cyano-3'-deoxy-5'-O-trityl-β-D-arabinofuranosyl)-thymine (VSB-025). Yield 31%. $R_f$ 0.47 (silica, ethylacetate).

b) A solution of 1-(3'-cyano-3'-deoxy-5'-O-trityl-β-D-arabino-furanosyl)-thymine (VSB-025; 200 mg) in acetic acid (8 ml) and water (2 ml) was heated at 80° C. for 15 min. Then, the solvent was evaporated and the residue purified on a silica gel column, using first chloroform as the eluent followed by chloroform:ethanol (9:1 v/v). The combined fractions were evaporated and the residue was triturated with hexane:ethanol (9:1 v/v) and gave 49 mg of the title compound VSB-026. Yield 60%. M.p. 219°–221° C. dec.

$^1$H-NMR (DMSO-$d_6$) δ: 1.75 (s, 3H, 5-CH$_3$), 3.23 (t, 1H, 3'-H), 3.50–3.80 (m, 2H, 5'-H), 4.09 (d, 1H, 4'-H), 4.72–4.86 (m (t on D$_2$O shake), 1H, 2'-H), 5.38 (t, 1H, 2'-OH), 6.10 (d, J=6.22 Hz, 1H, 1'-H), 6.34 (d, 1H, 5'-OH), 7.54 (s, 1H, 6-H), 11.30 (s, 1H, N—H).

EXAMPLE VII

Preparation of 1-(2'-3'-anhydro-β-D-lyxofuranosyl)-thymine (VSB-024)

1.5 g of 1-(2',3'-anhydro-5'-O-trityl-β-D-lyxofuranosyl)thymine (VSB-020) was treated with 80% acetic acid (10 ml) at +95° C. for 15 min. The solvent was then removed by evaporation and the residue was purified on a silica gel column using ethyl acetate as the eluent and 790 mg of the title compound VSB-024 was obtained. Yield 93%. M.p. 144°–146° C.

$^1$H-NMR (DMSO-$d_6$) δ: 1.80 (s, 3H, 5-CH$_3$), 3.60 (s, 1H, 5'-OH), 3.61 (d, 2H, 5'-H), 3.96–4.06 (m, 3H, 2'-H, 3'-H and 4'-H), 6.03 (s, 1H, 1'-H), 7.45 (s, 1H, 6-H), 11.20 (broad s, 1H, N—H).

EXAMPLE VIII

Preparation of 1-(3'-azido-3'-deoxy-β-D-arabinofuranosyl)thymine (VSB-022)

A suspension of 1'-(2',3'-anhydro-β-D-lyxofuranosyl)thymine (VSB-024; 268 mg), lithium azide (LiN$_3$; 110 mg), ammonium chloride (72 mg) in dry ethanol (25 ml) was refluxed for 24 hours. The solvent was then removed and the residue purified on a silica gel column (chloroform:ethanol 9:1 v/v) and 270 mg of the title compound was obtained. Further purification by trituration with hexane:ethanol (9.5:0.5 v/v) gave 217 mg of the title compound VSB-022. Yield 72%. M.p. 169.5°–170.5° C.

$^1$H-NMR (DMSO-$d_6$) δ: 1.77 (s, 3H, 5-CH$_3$), 3.60–3.75 (m, 3H, 4'-H and 5'H), 4.00 (t, 1H, 3'-H), 4.36 (q (t on D$_2$O shake), 1H, 2'-H), 5.30 (t, 1H, 5'-OH), 6.02 (d, J=6.23 Hz, 1H, 1'-H), 6.12 (d, 1H, 2'-OH), 7.61 (s, 1H, 6-H), 11.29 (s, 1H, N—H).

EXAMPLE IX

Preparation of 1-(3'-deoxy-3'-fluoro-β-D-arabinofuranosyl-thymine (VSB-027)

A mixture of 1'-(2',3'-anhydro-β-D-lyxofuranosyl)thymine (VSB-024; 367 mg), potassium hydrogenfluoride (586 mg) in dry ethane-1,2-diol (10 ml) was heated at +200° C. for 30 min. After cooling, the reaction mixture was directly applied to a silica gel column. The column was eluted with chloroform:ethanol (9:1 v/v), and 210 mg of the title compound (VSB-027) was obtained. Further purification by trituration with hexane : ethyl acetate gave 190 mg of VSB-027. Yield 48%. M.p. 162°–164° C. (EtOH).

$^1$H-NMR (DMSO-$d_6$) δ: 1.76 (s, 3H, 5-CH$_3$), 3.65 (t (d on D$_2$O shake), 2H, 5'-H), 4.04 (d, J 3'F, 4'=23 Hz, 1H, 4'-H), 4.34 (d, J 3'F, 2'=16 Hz, 1H, 2'-H), 4.97 (d, J3'F, 3'=53 Hz, 1H, 3'-H), 5.24 (t, 1H, 2'-OH), 6.00 (d, J4 Hz, 1H, 1'H), 7.43 (s, 1H, 6-H), 11.35 (s, 1H, N—H).

EXAMPLE X

Preparation of 1-(3'-fluoro-2'-methoxy-2',3'-dideoxy-β-D-arabino-furanosyl)thymine a) 90 mg 1-(5'-monomethoxytrityl-3'-deoxy-3'-fluoro-β-D-arabino-furanosyl)- 3-benzoyl thymine (0.14 mmol) was dissolved in 2 ml acetone. To the solutions was added 0.28 ml methyliodide (4.5 mmol) and 280 mg silveroxide (2.27 mmol). The reaction was stirred for 2 days. Then the mixture was filtered through celite and evaporated in vacuo. The product 1 -(5'-monomethoxytrityl-2',3'-dideoxy-3'-fluoro-2'-methoxy-β-D-arabino-furanosyl)- 3-benzoylthymine was isolated by chromatography on a silica gel column. Yield, 74 mg (81%). $^1$H-NMR (CDCl$_3$): 7.98-6.81 (m, 20 H, MMTr, Bz, H-6), 6.23 (dd, J$_{HF}$=1 Hz, J$_{1',2'}$=4.9 Hz. 1H, H-1'). 5.1 (dt, J$_{HF}$=52 Hz; H, H-3'). 4.21 (m, 1H, H-4'). 4.13 (m, 1H, H-2'). 3.81 (s, 3H, OMe of MMTr). 3.44 (d, 2H, H-5') 3.38 (s, 3H, 2'OMe). 1.74 (d, J=1 Hz, 3H, 5-CH$_3$).

b) 73 mg 1-(5'-monomethoxytrityl-2',3'-dideoxy-3'-fluoro-2'-methoxy-β -D-arabino-furanosyl)-3-benzoyl thymine (0.11 mmol) was treated with 5 ml saturated ammonia in methanol over night. Then the reaction mixture was evaporated, and dissolved in 3 ml 80% acetic acid. After 5 hour, it was dried in vacuo, and purified by chromatography on a silica gel column, yield 22 mg (73%). $^1$H-NMR (CDCl$_3$+CD$_3$OD): 7.43 (d, J=1.2 Hz, 1H, H-6), 6.22 (dd, J$_{HF}$=1.1 Hz, J$_{1'2'}$=4.9 Hz, 1H, H-1'). 5.13 (d, J$_{HF}$=52.5 Hz, 1H, H-3') 4.14 (m, 2H, H-2', H-4'). 3.84 (d, 2H, H-5) 3.39 (s, 3H, 2'-OMe), 1.91 (d, J=1.2 H, 5-CH$_3$). $^{13}$C-NMR (CDCl$_3$+CD$_3$OD): 164.3, (C-4), 150.5 (C-2), 137.4 (C-6), 109.4 (C-5), 97.3 and 89.1 (C-3', J$_{CF}$=186 Hz). 84.7 and 83.9 (C-1, J$_{CF}$=4.9 Hz). 82.9 and 81.8 (C-4', J$_{CF}$=24.4 Hz1) 82.1 and 81.0 (C-2', J$_{CF}$=24.4 Hz). 60.5 and 60.2 (C-5', J$_{CF}$=6.1 Hz). 58.5 (2'-OMe), 12.1 (5-Me).

The starting material for the compound of Example X was prepared in the following manner:

1) 260 mg (1 mmol) of 1-(3'-deoxy-3'-fluoro-β-D-arabinofuranosyl) thymine (Example IX) was dissolved in 10 ml pyridine. To the solution was added 0.75 ml trimethylchlorosilane (6 mmol). After 2 h, 0.35 ml benzoyl chloride (3 mmol) was added). The reaction was kept for 5 days. Then 30 drops of water was added to the reaction mixture, and the mixture was stirred for another 20 min. Then it was poured into saturated sodium hydrogen carbonate solution, and extracted with dichloromethane. The organic phase was evaporated and purified by chromatography on a silica gel column. Yield, 247 mg (68%): $^1$H-NMR (CDCl$_3$): 8.00-7.42 (m, 6H, Bz, H-6). 6.13 (t, J=3 Hz, 1H, H-1'), 5.04 (dt, J$_{HF}$=51 Hz, 1H, H-3'), 4.25 (m, 2H, H-2', H-4'), 3.93 (m, 2H, H-5'), 1.96 (d, J=1.2 Hz, 3H, 5-CH$_3$)

2) 230 mg 1-(3'-deoxy-3'-fluoro-β-D-arabinofuranosyl)-3-benzoylthymine (0.63 mmol) was dissolved in pyridine. To the solution was added 308 mg monomethoxytrityl chloride (1 mmol). After reaction overnight, 5 ml methanol was added and the mixture was worked up with sodium hydrogen carbonate solution and extracted by dichloromethane. The organic phase was dried in vacuo, and the product was isolated from silica gel column chromatography. Yield 248 mg (62%). $^1$H-NMR (CDCl$_3$): 8.00-6.82 (m, 20 H, MMTr, Bz, H-6). 6.13 (dd, J$_{HF}$=1.2 Hz, J$_{1'2'}$=3.8 Hz, 1H, H-1'). 4.00 (dt, J$_{HF}$=51.5 Hz, 1H, H-3'). 4.53 (m, 2H, H-2', H-4'). 3.81 (s, 3H, OMe). 3.50 (m, 2H, H-5'). 1.77 (d, J=1.2 Hz, 5-CH$_3$).

EXAMPLE XI

Preparation of 1-(3'-azido-2'-methoxy-2',3'-dideoxy-β-D-arabino-furanosyl)thymine a) 90 mg 1(-5'-monomethoxytrityl-3'-deoxy-3'-azido-β-D-arabino-furanosyl)- 3-benzoylthymine (0.14 mmol) was dissolved in dry acetone 1.5 ml. To the solution 280 mg silveroxide (2.27 mmol) and 0.28 ml methyliodide (4.5 mmol) was added. The suspension was stirred for 3 days. After filtration through celite and evaporation, the product was purified by silica gel column chromatography. Yield: 71 mg (77%). $^1$H-NMR (CDCl$_3$): 8.00-6.82 (m, 20 H, MMTr, Bz, H-6), 6.22 (d, J=5.6 Hz, 1H, H-1'). 4.21 (dd, J=6 Hz, 1H, H-3'), 3.98 (t, J=5.7 Hz, 1H, H-2'), 3.83 (m, 1H, H-4'), 3.81 (s, 3H, OMe of MMTr). 3.52 (m, 2H, H-5'), 3.42 (s, 3H, 2'-OMe), 1.66 (d, J=1.3 Hz, 3H, 5-CH$_3$).

b) 70 mg 1-(5'-monomethoxytrityl-2',3'-dideoxy-3'-azido-2'-methoxy-β -D-arabinofuranosyl)-3-benzoylthymine was treated with 3 ml saturated ammonia in methanol over-night. The volatile material was removed by evaporation in vacuo. The residue was dissolved in 3 ml 80 % acetic acid for 4 h. After evaporation in vacuo, the product was isolated by chromatography on a silica gel column. 23 mg (74%). $^1$H-NMR (CDCl$_3$): 9.23 (broad s, 1H, NH), 7.43 (d, J=1.2 Hz, 1H, H-6), 6.25 (d, J=5.6 Hz, 1H, H-1'). 4.25-3.7 (m 5H, H-2', H-3', H-4', H-5'), 3.40 (s, 3H, 2'-OMe). 1.90 (d, J=1.2 H, 3H, 5-CH3). $^{13}$C-NMR (CDCl$_3$): 164.0 (C-4), 150.5 (C-2), 137.3 (C-6), 109.9 (C-5), 84.6 (C-1'), 82.8 (C-4'), 79.8 (C-2'), 62.7 (C-3'), 59.9 (C-5'), 59.1 (2'-OMe), 12.27 (5 -CH$_3$).

The starting material for the compound of Example XI was prepared in the following manner:

1) 120 mg 1-(3'-azido-3'-deoxy-β-D-arabinofuranosyl)thymine (Example VIII) (0.42 mmol) was dissolved in 5 ml pyridine. To the solution was added 200 mg monomethoxytrityl chloride (0.63 mmol). After reaction for 18 hours 5 ml methanol was added. Then the reaction mixture was worked up with saturated sodium hydrogen carbonate and extracted with methylene chloride. The organic phase was evaporated and applied to chromatography on a silica gel column. Yield: 210 mg (90%). $^1$H-NMR (CDCl$_3$): 7.59-6.80 (m, 15 H, MMTr, H-6), 6.10 (d, J=5.1 Hz, 1H, H-1'). 4.52 (t, J=5.1 Hz, 1H, H- 2'). 4.13 (t, J=5.3 Hz, 1H, H-3'). 3.86 (m, 1H, H-4'), 3.78 (s, 3H, OMe). 3.46 (m, 2H, H-5'), 1.60 (d, J=1 Hz, 3H, 5-CH$_3$)

2) 200 mg 1-(5'-monomethoxytrityl-3'-azido-3'-deoxy-β-D-arabinofuranosyl)thymine (0.36 mmol) was dissolved in pyridine. To the solution was added 0.18 ml trimethylchlorosilane (1.4 mmol). After 1 h, 0.12 ml benzoylchloride (1 mmol) was added. The reaction was kept for 5 days. Then 15 drops of water was added. After stirring for 20 rain, the reaction was worked up with aqueous sodium hydrogen carbonate solution. The product was isolated by silica gel short column chromatography. Yield 98 mg (42%). $^1$H-NMR (CDCl$_3$): 7.98-6.82 (m, 20H, MMTr, Bz, H-6), 6.05 (d, J=5.2 Hz, 1H, H-1'), 4.45 (m, 1H, H-2'), 4.16 (t, J=7 Hz, 1H, H-3'), 3.90 (m, 1H, H-4'), 3.81 (s, 3H, OMe), 3.57 (m, 2H, H-5'), 1.64 (d, J=1.2 Hz, 3H, 5-CH$_3$).

EXAMPLE XII

Preparation of 1-[2,3-Dideoxy-3-C-ethynyl-β-D-erythro-pentofuranosyl]thymine (MSC-015)

To a solution of KOH (35 mg, 0.60 mmol) in n-propanol (2 ml) was added a solution of MSC-014 (78 mg, 0.14 mmol) in n-propanol (2 ml). The reaction mixture was refluxed for 15 h and diluted with EtOAc (50 ml). The organic phase was washed with saturated NH$_4$Cl-solution (20 ml) and water (20 ml), dried (Na$_2$SO$_4$). The solvent was removed and the residue was purified on silica gel using EtOAc as the eluent. 13 mg (20 %) of a α,β-mixture of protected MSC-015 was obtained. $^1$H-NMR in CDCl$_3$ showed two doublets (J=0.74 Hz) at 2.17 ppm (—C≡C—H). The protecting group was removed by treating the above described α,β-mixture (13 mg, 0.026 mmol) with a solution of tetrabutylammonium fluoride (21 mg, 0.067 mmol) in THF (3 ml). The reaction mixture was stirred at room temperature for 1.5 h. The solvent was evaporated in vacuo and the residue purified on SiO$_2$ with EtOAc as the eluent. This procedure afforded 2.5 mg (39%) of MSC-015. $^{13}$C-NMR (CDCl$_3$)δ: 12.72, 28.82, 39.27, 61.07, 71.56, 81.58, 85.79, 85.90, 111.06, 136.44, 150.35. Carbon atom No. 4 in the thymine base was not detected.

The starting material for the compound of Example XII was prepared in the following manner:

EXAMPLE 1

5-O-(tert-Butyldiphenylsilyl)-2,3-dideoxy-D-glycero-pent-2-enono-1,4-lactone (MSC-006)

To a solution of (S)-5-hydroxy-2-penten-4-olide [3.2 g, 28.07 mmol; prepared from 1,2:5,6-di-O-isopropylidene-D-mannitol (Aldrich) in a 3-step sequence described by Häfele and Jäger in Liebigs Ann. Chem. 1987, 85–87], in dry DMF (50 ml), at 0° C., was added imidazole (2.95 g, 42.1 mmol), followed by tert-butylchlorodiphenylsilane (7.95 ml, 30.9 mmol). The cooling bath was removed and the reaction mixture was stirred at room temperature for a period of 1 h. Then, the solvent was evaporated and the residue was purified on a silica gel column using hexane/EtOAc (7:3 v/v) as the eluent. The appropriate fractions were evaporated and gave 9.0 g (91%) of MSC-006. $^{13}$C-NMR (CDCl$_3$)δ: 19.40, 26.88, 63.53, 83.40, 122.89, 128.05, 130.20, 132.68, 132.95, 135.71, 135.76, 154.20. (The carbonyl carbon was not detected).

EXAMPLE 2

5-O-(tert-Butyl-diphenylsilyl)-2,3-dideoxy-3-C-vinyl-D-erythro-pentono-1,4-lactone (MSC-008)

To a deoxygenated suspension of copper(I)bromide-dimethyl sulfide complex (411 mg, 2 mmol) in dry THF (60 ml) and dry diethyl ether (20 ml), at −40° C. and under nitrogen, was added vinylmagnesium bromide (20 ml of a 1 M solution in THF, 20 mmol). The reaction mixture was stirred at about −35° C. for 30 min, whereafter a solution of MSC-006 (3.5 g, 10 mmol) in dry THF (10 ml) was added. The reaction mixture was stirred and the temperature was allowed to slowly reach room temperature. After 3 h, when the temperature was +5° C., the starting material was consumed according to tlc. The reaction mixture was then poured into saturated NH$_4$Cl-solution (200 ml) and extracted with EtOAc (3×200 ml). The organic phase was washed with saturated NH$_4$Cl-solution (150 ml) and water (150 ml) and dried over Na$_2$SO$_4$. The solvent was evaporated and the residue purified on a silica gel column using hexane/EtOAc (7:2 v/v) as the eluent. This gave 2.58 g (68%) of the desired title compound (MSC 008). $^{13}$C-NMR (CDCl$_3$)δ: 19.44, 26.95, 35.29, 40.96, 63.56, 84.79, 117.62, 128.04, 129.84, 130.11, 135.76, 135.85, 136.64. (The carbonyl carbon was not detected).

EXAMPLE 3

5-O-(tert-Butyldiphenyl)-2,3-dideoxy-3-C-vinyl-D-erythro-pentofuranose (MSC-009)

To a deoxygenated solution of MSC-008 (2.58 g, 6.78 mmol) in dry CH$_2$Cl$_2$ (100 ml), at −70° C. and under nitrogen, was added diisobutyl-aluminium hydride (8.7 ml of a 1.1M solution in hexane, 9.54 mmol). The reaction mixture was stirred for about 2 h at −70° C. Then, the reaction was quenched by the addition of CH$_3$OH (300 ml) and stirred at +20° C. for 2 h. The resulting white precipitate was filtered off and washed with CH$_3$OH. Evaporation of the combined fractions gave a crude product which was purified on a silica gel column using hexane/EtOAc (5:1 v/v) as the eluent. 2.17 g (84%) MSC-009 was obtained. $^{13}$C-NMR (CDCl$_3$)δ: 19.40, 27.06, 40.46, 41.60, 41.88, 44.35, 64.48, 83.56, 85.03, 98.63, 99.05, 115.83, 116.41, 127.82, 127.97, 129.80, 130.03, 130.09, 133.00, 135.84, 135.94, 138.37, 139.39.

EXAMPLE 4

1-O-Acetyl-5-O-(tert-butyldiphenylsilyl)-2,3-dideoxy-3-C-vinyl-α,β-D-erythro-pentofuranose (MSC-010)

To a solution of MSC-009 (2.0 g, 5.2 mmol) in dry pyridine (15 ml), at room temperature, was added acetic anhydride (1.0 ml, 10.5 mmol). The reaction mixture was stirred at room temperature for 60 h. The solvent was carefully removed and the residue was dissolved in EtOAc (200 ml). The organic phase was washed with saturated K$_2$CO$_3$-solution (50 ml) and water (50 ml). Drying (Na$_2$SO$_4$) and evaporation of the solvent gave a crude product which was purified on silica gel using hexane/EtOAc (1:9 v/v) as the eluent. This procedure gave 1.95 g (89%) of MSC-010. $^{13}$C-NMR (CDCl$_3$)δ: 19.44, 21.50, 26.71, 26.94, 39.03, 39.36, 42.16, 43.53, 64.12, 64.39, 85.50, 86.33, 98.29, 99.40, 115.99, 117.10, 127.81, 129.81, 133.45, 133.61, 135.76, 137.11, 139.16.

EXAMPLE 5

1-[5-O-(tert-Butyldiphenylsilyl)-2,3-dideoxy-3-C-vinyl-α,β-D-erythropentofuranosyl] thymine (MSC-011)

A suspension of thymine (693 mg, 5.5 mmol), chlorotrimethylsilane (5 drops) and (NH$_4$)$_2$SO$_4$ (a few mg) in hexamethyldisilazane (10 ml) was refluxed for 5 h. The reaction solution was filtered and evaporated to give crude bistrimethylsilylated thymine, which was dissolved in dry 1,2-dichloroethane (10 ml). To this solution, deoxygenated and under nitrogen, was added a solution of MSC-010 (1.8 g, 4.25 mmol) in 1,2-dichloroethane (10 ml) followed by tert-butyldimethylsilyl trifluoromethanesulfonate (1.15 ml, 5 mmol). The reaction mixture was stirred for 15 h, diluted with CH$_2$Cl$_2$ (150 ml), washed with saturated K$_2$CO$_3$-solution (50 ml) and water (50 ml), and dried (Na$_2$SO$_4$). The solvent was removed in vacuo and the residue was purified by column chromatography using a SiO$_2$-column eluted with hexane/EtOAc (2:1 v/v) 1.65 g (79%) of the title compound was obtained. $^{13}$C-NMR (CDCl$_3$)δ: 12.23, 12.77, 19.40, 19.58, 26.95, 27.15, 39.39, 39.51, 41.80, 43.97, 62.78, 63.92, 84.84, 85.38, 85.62, 86.56, 110.81, 117.49, 117.83, 127.86, 127.98, 128.93, 129.90, 130.06, 133.37, 135.14, 135.48, 135.74, 136.16, 136.33, 150.50, 164.17.

EXAMPLE 6

1-[5-O-(tert-Butyldiphenylsilyl)-3-C-(1,2-dibromoethyl)-2,3-dideoxy-δ,β-D-erythro-pentofuranosyl] thymine (MSC-012)

To a solution of MSC-011 (550 mg, 1.12 mmol) in 30 ml CCl$_4$, at −20° C., was added bromine (59 μl, 1.15 mmol). The reaction mixture was stirred for 1.5 h whereupon the reaction temperature slowly reached room temperature. The solvent was evaporated and the crude product was purified on silica gel using hexane/EtOAc (7:3 v/v) as the eluent. 310 mg (43%) of MSC-012 was obtained. $^{13}$C-NMR (CDCl$_3$)δ: 12.34, 12.85, 19.33, 1949, 26.99, 27.17, 33.38, 33.53, 33.90, 34.11, 40.49, 42.74, 52.71, 54.11, 62.95, 64.63, 83.06, 83.73, 84.58, 85.55, 111.29, 128.01, 128.15, 130.10, 130.19, 130.29, 132.92, 135.02, 135.25, 135.54, 135.75, 150.38, 163.82.

EXAMPLE 7

1-[3-C-(1-Bromoethenyl)-5-O-tert-butyldiphenylsilyl)-2,3-dideoxy-α,β-D-erythro-pentofuranosyl] thymine (MSC-014)

To a solution of Na (68 mg, 2.9 mmol) in $CH_3OH$ (6 ml) was added a solution of MSC 012 (310 mg, 0.48 mmol) in 4 ml of $CH_3OH$. The reaction mixture was then stirred at room temperature for 15 h. The solvent was evaporated and the residue was partitioned between EtOAc (150 ml) and saturated $NH_4Cl$-solution (100 ml). The organic phase was washed with water (100 ml) and dried ($Na_2SO_4$). The solvent was evaporated and the residue purified on silica gel using pentane/EtOAc (7:3 v/v) as the eluent. 235 mg (85%) of MSC 014 was obtained. $^{13}$C-NMR ($CDCl_3$)δ: 12.22, 12.85, 19.39, 19.59, 26.97, 27.04, 27.17, 38.33, 38.66, 47.31, 48.95, 62.60, 63.66, 83.38, 83.75, 84.58, 85.73, 111.11, 119.68, 120.03, 127.93, 128.05, 128.09, 128.35, 130.01, 130.16, 130.22, 132.62, 135.04, 135.36, 135.45, 135.62, 135.72, 150.38, 163.91.

EXAMPLE XIII

Preparation of 1-(3'-ethynyl-2'-methoxy-2',3'-dideoxy-β-D-arabino-furanosyl)thymine 140 mg 1-(5'-trityl-3'-ethynyl-3'-deoxy-β-D-arabinofuranosyl)-3-benzoylthymine (0.23 mmol) was dissolved in 3 ml acetone. To the solution was added 0.43 ml MeI (6.9 mmol) and 425 mg silveroxde (3.45 mmol). The suspension was stirred for 3 days. After filtration through celite, the filtrate was evaporated. The residue was treated with 10 ml 0.5M NaOMe in methanol for 2 h. After cooling down, it was neutralized with acetic acid. The solution was evaporated. To the residue was added 3 ml acetic acid and 1 ml water. The reaction was treated to 90° C. for 15 min. After cooling down, it was evaporated, and purified by silica gel column chromatography. Yield: 19 mg (30%). $^1$H-NMR($CDCl_3$+$CD_3OD$): 7.57 (d, J=1.2 Hz, 1H, H-6). 6.25 (d, J=5.9 Hz, 1H, H-1'), 4.20 (dd, $J_{2',3'}$=6.8 Hz, 1H, H-2'), 3.90 (m, 3H, H-4', H-5'), 3.43 (s, 3H, 2'-OMe), 3.07 (m, 1H, H-3'), 2.32 (d, J=2.4 Hz, 1H, C≡CH), 1.99 (d, J=1.2 Hz, 3H, 5-Me). $^{13}$C-NMR ($CDCl_3$+$CD_3OD$): 164.3 (C-4), 150.5 (C-2), 137.5 (C-6), 109.4 (C-5), 85.3 (C-1'), 83.2 (C-4'), 81.4 (C-2'), 80.2 (—C≡), 72.2 (≡CH), 59.9 (C-5'), 58.9 (2'-OMe), 35.6 (C-3'), 12.0 (5-$CH_3$).

The starting material for the compound of Example XIII was prepared in the following manner:

254 mg 1-(5'-trityl-3'-ethynyl-3'-deoxy-β-D-arabinofuranosyl)thymine (0.5 mmol) (Example Va) was dissolved in 7 ml pyridine. To the solution was added 0.19 ml trimethylchlorosilane (1.5 mmol). After 2 h, 0.18 ml benzoylchloride (1.5 mmol) was added. The reaction was kept for 3 days. Then 4 ml methanol was added. The mixture was stirred for 30 min and poured in saturated $NaHCO_3$ solution and extracted with dichloromethane. The product was purified by silica gel column chromatography. Yield 202 mg (66 %). $^1$H-NMR($CDCl_3$): 7.99-7.17 (m, 21H, Tr, Bz, H-6), 6.09(d, J=5.3 Hz, 1H, H-1'), 4.60 (m, 1H, H-2'), 4.04 (m, 1H, H-4'), 3.53 (m, 2H, H-5'), 3.29 (m, 1H, H-3'), 2.24 (d, J=2.4 Hz, 1H, ≡CH), 1.59 (d, J=1.2 Hz, 3H, 5-$CH_3$).

The compounds of the present invention and at least one of their respective reaction schemes for the preparation of the compounds are reproduced in the Table hereinbelow.

TABLE

COMPOUNDS OF INTEREST

| Example | $R^1$ | $R^2$ | $R^3$ | $R^4$ | $R^5$ | $R^6$ | $R^7$ | Reaction scheme no. |
|---|---|---|---|---|---|---|---|---|
| III | OH | $CH_2CH_2CH_3$ | | | H | F | OH | |
| V | OH | $CH_3$ | | | OH | C≡CH | OH | 3, 4a |
| VI | OH | $CH_3$ | | | OH | CN | OH | 3, 4a |
| VIII | OH | $CH_3$ | | | OH | $N_3$ | OH | 3, 4a |
| IX | OH | $CH_3$ | | | OH | F | OH | 3, 4a |
| X | OH | $CH_3$ | | | $OCH_3$ | F | OH | 3, 1 |
| XI | OH | $CH_3$ | | | $OCH_3$ | $N_3$ | OH | 4a, 1 |
| XII | OH | $CH_3$ | | | H | C≡CH | OH | 2 |
| XIII | OH | $CH_3$ | | | $OCH_3$ | C≡CH | OH | 4a, 1 |
| XIV | OH | Br | | | H | F | OH | 6 |
| XV | OH | I | | | H | F | OH | 6 |
| XVI | OH | Cl | | | H | F | OH | 6 |
| XVII | OH | $CH_3$ | | | OH | $OCH_3$ | OH | 4a |
| XVIII | OH | $CH_3$ | | | $OCH_3$ | $OCH_3$ | OH | 4a |
| XIX | OH | $CH_3$ | | | $OCH_3$ | CN | OH | 4a |
| XX | OH | $CH_3$ | | | OH | H | OH | 3, 4a |
| XXI | OH | $CH_3$ | | | $OCH_3$ | H | OH | 4a |
| XXII | OH | $CH_3$ | | | $OCH_3$ | F | $OCH_3$ | 5 |
| XXIII | OH | $CH_2CH=CH_3$ | | | $OCH_3$ | F | OH | 4a |
| XXIV | $NH_2$ | H | | | OH | H | OH | 3, 4b |
| XXV | $NH_2$ | H | | | $OCH_3$ | H | OH | 4b |
| XXVI | $NH_2$ | H | | | OH | F | OH | 3, 4b |
| XXVII | $NH_2$ | H | | | $OCH_3$ | F | OH | 4b |
| XXVIII | $NH_2$ | H | | | $OCH_3$ | F | $OCH_3$ | 5 |
| XXIX | $NH_2$ | H | | | OH | $OCH_3$ | OH | 3, 4b |
| XXX | $NH_2$ | H | | | $OCH_3$ | $OCH_3$ | OH | 4b |
| XXXI | $NH_2$ | B | | | OH | CN | OH | 3, 4b |
| XXXII | $NH_2$ | H | | | $OCH_3$ | CN | OH | 4b |
| XXXIII | $NH_2$ | H | | | OH | C≡CH | OH | 3, 4b |
| XXXIV | $NH_2$ | H | | | $OCH_3$ | C≡CH | OH | 4b |
| XXXV | $NH_2$ | H | | | OH | $N_3$ | OH | 3, 4b |

TABLE-continued

COMPOUNDS OF INTEREST

| Example | R¹ | R² | R³ | R⁴ | R⁵ | R⁶ | R⁷ | Reaction scheme no. |
|---|---|---|---|---|---|---|---|---|
| XXXVI | NH$_2$ | H | | | OCH$_3$ | N$_3$ | OH | 4b |
| XXXVII | NH$_2$ | H | | | H | OCH$_3$ | OH | 7 |
| XXXVIII | NH$_2$ | H | | | H | C≡CH | OH | 7 |
| XXXIX | OH | H | | | OH | F | OH | 4a |
| XLI | OH | H | | | OCH$_3$ | F | OH | 4a |
| XLII | OH | H | | | OCH$_3$ | F | OCH$_3$ | 5 |
| XLIII | | | OH | NH$_2$ | OH | H | OH | 3, 4c |
| XLIV | | | OH | NH$_2$ | OCH$_3$ | H | OH | 4c |
| XLV | | | OH | NH$_2$ | OH | F | OH | 3, 4c |
| XLVI | | | OH | NH$_2$ | OCH$_3$ | F | OH | 4c |
| XLVII | | | OH | NH$_2$ | OH | F | OCH$_3$ | 5 |
| XLVIII | | | OH | NH$_2$ | OCH$_3$ | F | OCH$_3$ | 5 |
| XLIX | | | OH | NH$_2$ | OH | OCH$_3$ | OH | 3, 4c |
| L | | | OH | NH$_2$ | OCH$_3$ | OCH$_3$ | OH | 4c |
| LI | | | OH | NH$_2$ | OH | CN | OH | 3, 4c |
| LII | | | OH | NH$_2$ | OCH$_3$ | CN | OH | 4c |
| LIII | | | OH | NH$_2$ | OH | C≡CH | OH | 3, 4c |
| LIV | | | OH | NH$_2$ | OCH$_3$ | C≡CH | OH | 4c |
| LV | | | OH | NH$_2$ | OH | N$_3$ | OH | 3, 4c |
| LVI | | | OH | NH$_2$ | OCH$_3$ | N$_3$ | OH | 4c |
| LVII | | | H | NH$_2$ | OH | F | OH | 3, 4d |
| LVIII | | | H | NH$_2$ | OCH$_3$ | F | OH | 4d |
| LIX | | | NH$_2$ | NH$_2$ | OH | F | OH | 3, 4d |
| LX | | | NH$_2$ | NH$_2$ | OCH$_3$ | F | OH | 4d |
| LXI | | | NH$_2$ | H | OH | H | OH | 3, 4d |
| LXII | | | NH$_2$ | H | OCH$_3$ | H | OH | 4d |
| LXIII | | | NH$_2$ | H | OH | F | OH | 4d |
| LXIV | | | NH$_2$ | H | OCH$_3$ | F | OH | 4d |
| LXV | | | NH$_2$ | H | OH | F | OCH$_3$ | 5 |
| LXVI | | | NH$_2$ | H | OCH$_3$ | F | OCH$_3$ | 5 |
| LXVII | | | NH$_2$ | H | OH | OCH$_3$ | OH | 3, 4d |
| LXVIII | | | NH$_2$ | H | OCH$_3$ | OCH$_3$ | OH | 4d |
| LXIX | | | NH$_2$ | H | OH | CN | OH | 3, 4d |
| LXX | | | NH$_2$ | H | OCH$_3$ | CN | OH | 4d |
| LXXI | | | NH$_2$ | H | OH | C≡CH | OH | 3, 4d |
| LXXII | | | NH$_2$ | H | OCH$_3$ | C≡CH | OH | 4d |
| LXXIII | | | NH$_2$ | H | OH | N$_3$ | OH | 3, 4d |
| LXXIV | | | NH$_2$ | H | OCH$_3$ | N$_3$ | OH | 4d |
| LXXV | | | OH | H | OH | H | OH | 3, 4f |
| LXXVI | | | OH | H | OCH$_3$ | H | OH | 4f |
| LXXVII | | | OH | H | OH | F | OH | 3, 4f |
| LXXVIII | | | OH | H | OCH$_3$ | F | OH | 4f |
| LXXIX | | | OH | H | OH | F | OCH$_3$ | 5 |
| LXXX | | | OH | H | OCH$_3$ | F | OCH$_3$ | 5 |
| LXXXI | | | OH | H | OH | OCH$_3$ | OH | 3, 4f |
| LXXXII | | | OH | H | OCH$_3$ | OCH$_3$ | OH | 4f |
| LXXXIII | | | OH | H | OH | CN | OH | 3, 4f |
| LXXXIV | | | OH | H | OCH$_3$ | CN | OH | 4f |
| LXXXV | | | OH | H | OH | C≡CH | OH | 3, 4f |
| LXXXVI | | | OH | H | OCH$_3$ | C≡CH | OH | 4f |
| LXXXVII | | | OH | H | OH | N$_3$ | OH | 3, 4f |
| LXXXVIII | | | OH | H | OCH$_3$ | N$_3$ | OH | 4f |
| LXXXIX | | | OH | OH | OH | H | OH | 3, 4e |
| XC | | | OH | OH | OCH$_3$ | H | OH | 4e |
| XCI | | | OH | OH | OH | F | OH | 3, 4e |
| XCII | | | OH | OH | OCH$_3$ | F | OH | 4e |
| XCIII | | | OH | OH | OH | F | OCH$_3$ | 5 |
| XCIV | | | OH | OH | OCH$_3$ | F | OCH$_3$ | 5 |
| XCV | | | OH | OH | OH | OCH$_3$ | OH | 3, 4e |
| XCVI | | | OH | OH | OCH$_3$ | OCH$_3$ | OH | 4e |
| XCVII | | | OH | OH | OH | CN | OH | 3, 4e |
| XCVIII | | | OH | OH | OCH$_3$ | CN | OH | 4e |
| XCIX | | | OH | OH | OH | C≡CH | OH | 3, 4e |
| C | | | OH | OH | OCH$_3$ | C≡CH | OH | 4e |
| CI | | | OH | OH | OH | N$_3$ | OH | 3, 4e |
| CII | | | OH | OH | OCH$_3$ | N$_3$ | OH | 4e |
| CIII | | | OH | NH$_2$ | H | OCH$_3$ | OH | 7 |
| CIV | | | OH | NH$_2$ | H | CN | OH | 7 |
| CV | | | OH | NH$_2$ | H | C≡CH | OH | 7 |
| CVI | | | NH$_2$ | H | H | OCH$_3$ | OH | 7 |
| CVII | | | NH$_2$ | H | H | CN | OH | 7 |
| CVIII | | | NH$_2$ | H | H | C≡CH | OH | 7 |
| CIX | | | OH | H | H | F | OH | 7 |
| CX | | | OH | H | H | OCH$_3$ | OH | 7 |

TABLE-continued
COMPOUNDS OF INTEREST

| Example | $R^1$ | $R^2$ | $R^3$ | $R^4$ | $R^5$ | $R^6$ | $R^7$ | Reaction scheme no. |
|---|---|---|---|---|---|---|---|---|
| CXI | | | OH | H | H | CN | OH | 7 |
| CXII | | | OH | H | H | C≡CH | OH | 7 |
| CXIII | | | OH | OH | H | F | OH | 7 |
| CXIV | | | OH | OH | H | $OCH_3$ | OH | 7 |
| CXV | | | OH | OH | H | CN | OH | 7 |
| CXVI | | | OH | OH | H | C≡CH | OH | 7 |
| CXVII | OH | $CH_3$ | | | OH | H | F | 5 |
| CXVIII | OH | $CH_3$ | | | $OCH_3$ | H | F | 5 |
| CXIX | OH | $CH_3$ | | | OH | F | F | 5 |
| CXX | OH | $CH_3$ | | | $OCH_3$ | F | F | 5 |
| CXXI | $NH_2$ | H | | | OH | H | F | 5 |
| CXXII | $NH_2$ | H | | | $OCH_3$ | H | F | 5 |
| CXXIII | | | OH | $NH_2$ | OH | H | F | 5 |
| CXXIV | | | OH | $NH_2$ | $OCH_3$ | H | F | 5 |
| CXXV | | | OH | $NH_2$ | OH | F | F | 5 |
| CXXVI | | | OH | $NH_2$ | $OCH_3$ | F | F | 5 |
| CXXVII | | | $NH_2$ | H | OH | H | F | 5 |
| CXXVIII | | | $NH_2$ | H | $OCH_3$ | H | F | 5 |
| CXXIX | | | OH | H | OH | H | F | 5 |
| CXXX | | | OH | H | $OCH_3$ | H | F | 5 |
| CXXXI | | | OH | OH | OH | H | F | 5 |
| CXXXII | | | OH | OH | $OCH_3$ | H | F | 5 |

REACTION SCHEME 3.

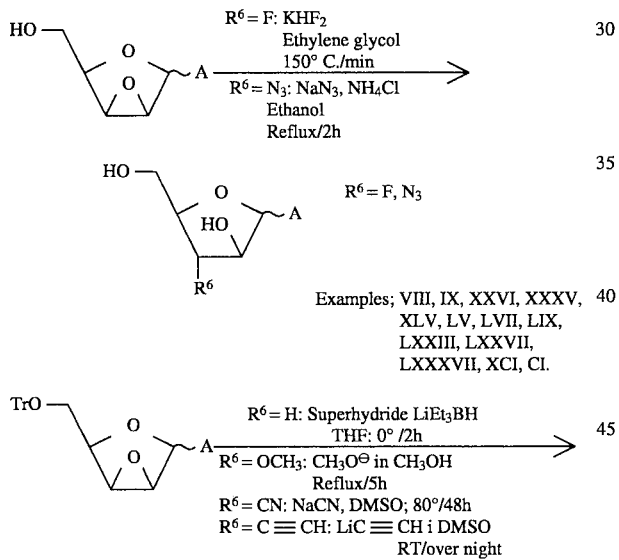

Examples; VIII, IX, XXVI, XXXV, XLV, LV, LVII, LIX, LXXIII, LXXVII, LXXXVII, XCI, CI.

-continued
REACTION SCHEME 3.

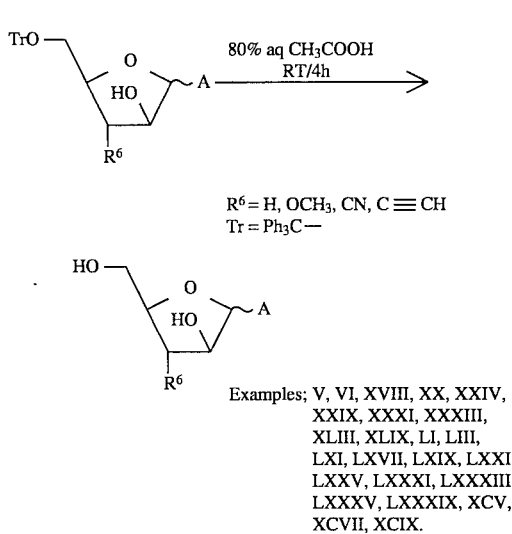

Examples; V, VI, XVIII, XX, XXIV, XXIX, XXXI, XXXIII, XLIII, XLIX, LI, LIII, LXI, LXVII, LXIX, LXXI, LXXV, LXXXI, LXXXIII, LXXXV, LXXXIX, XCV, XCVII, XCIX.

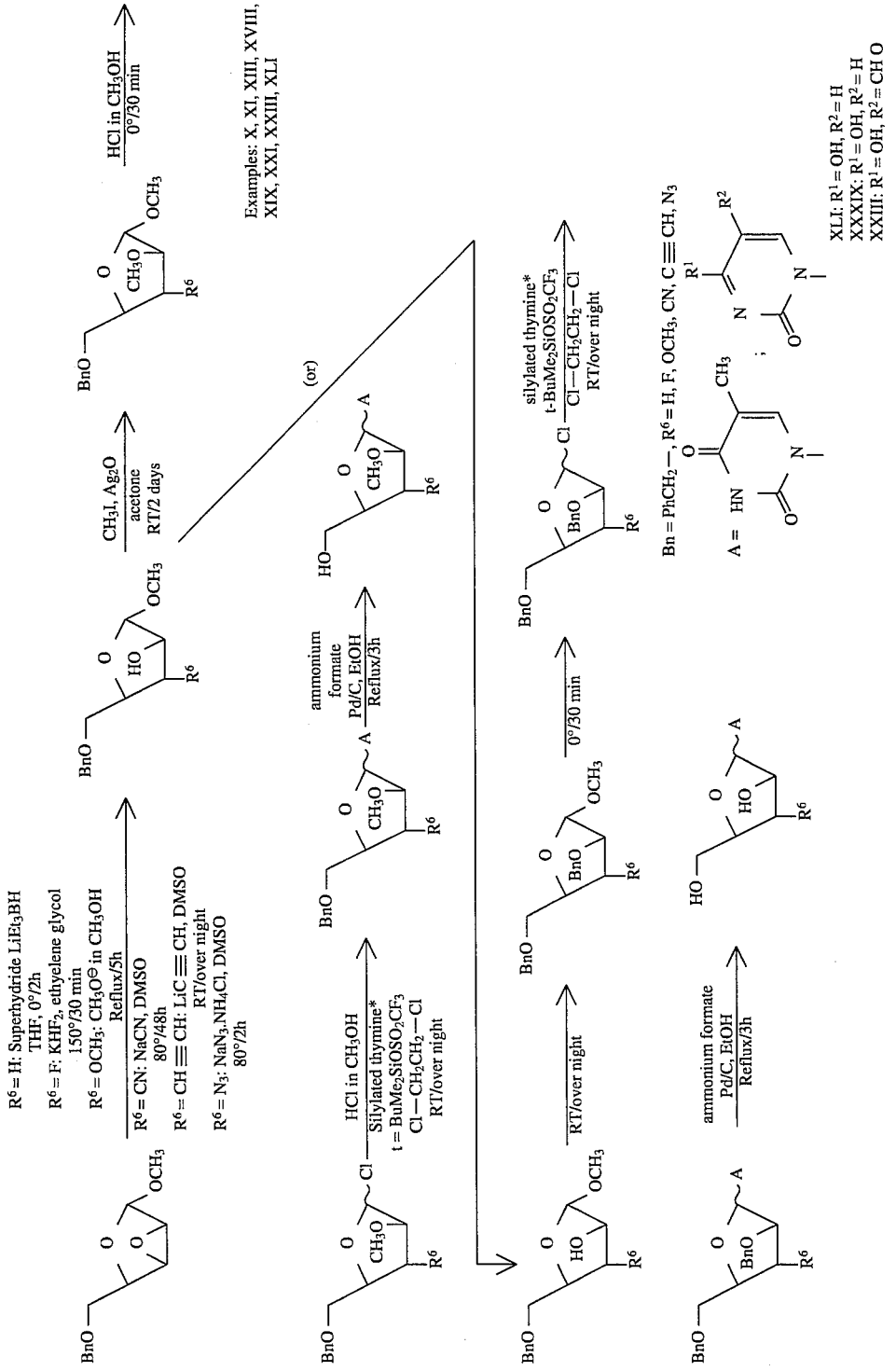

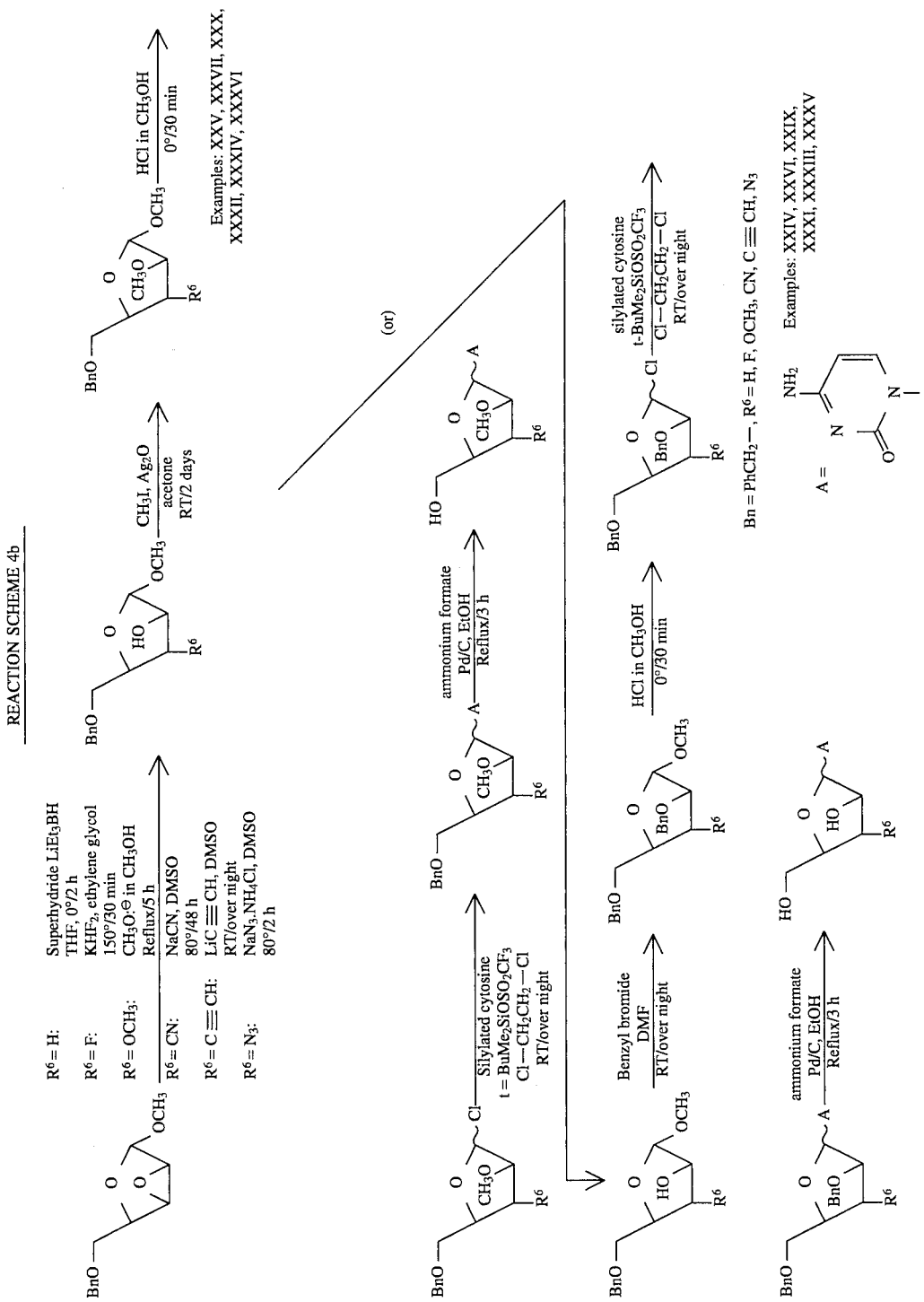

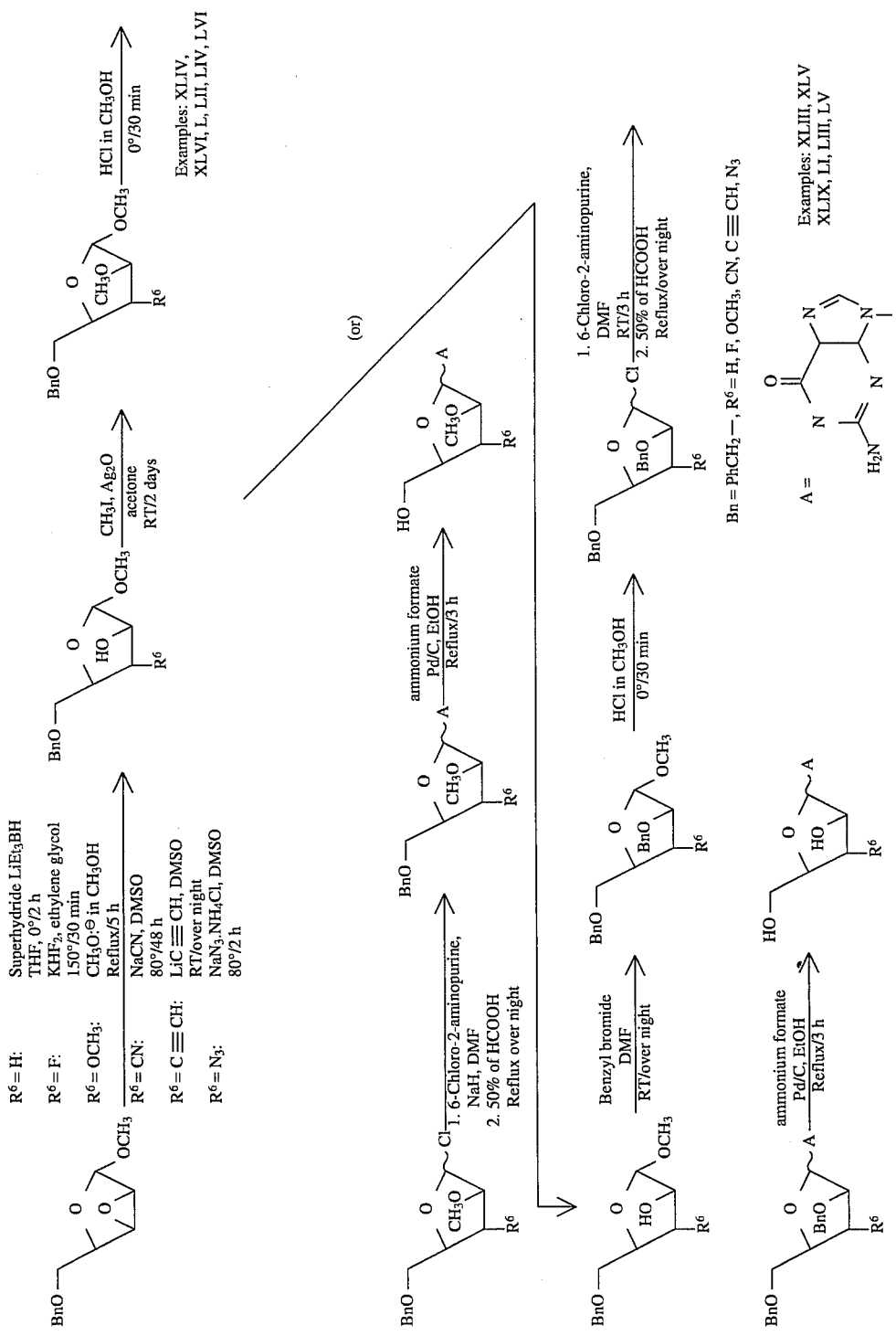

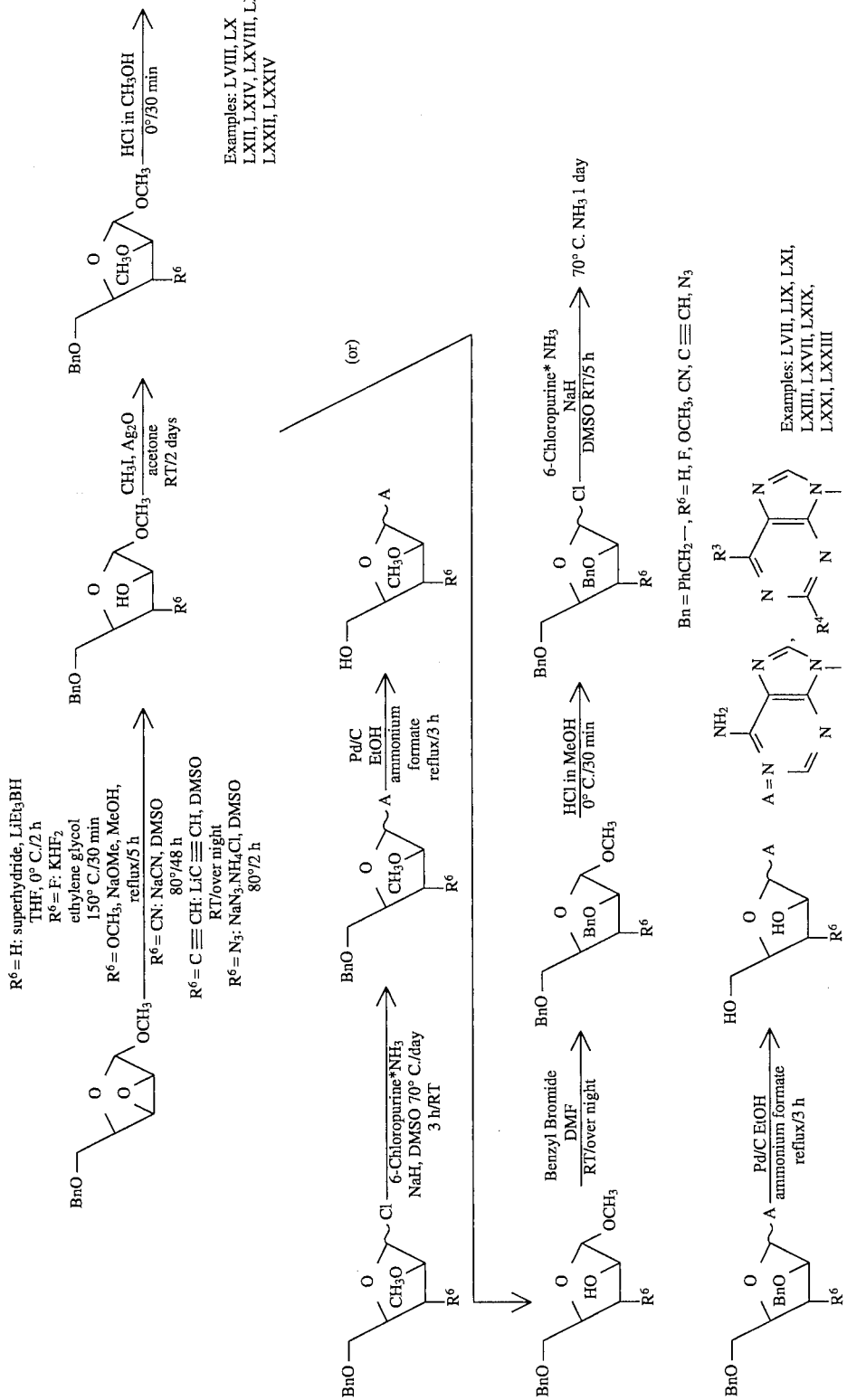

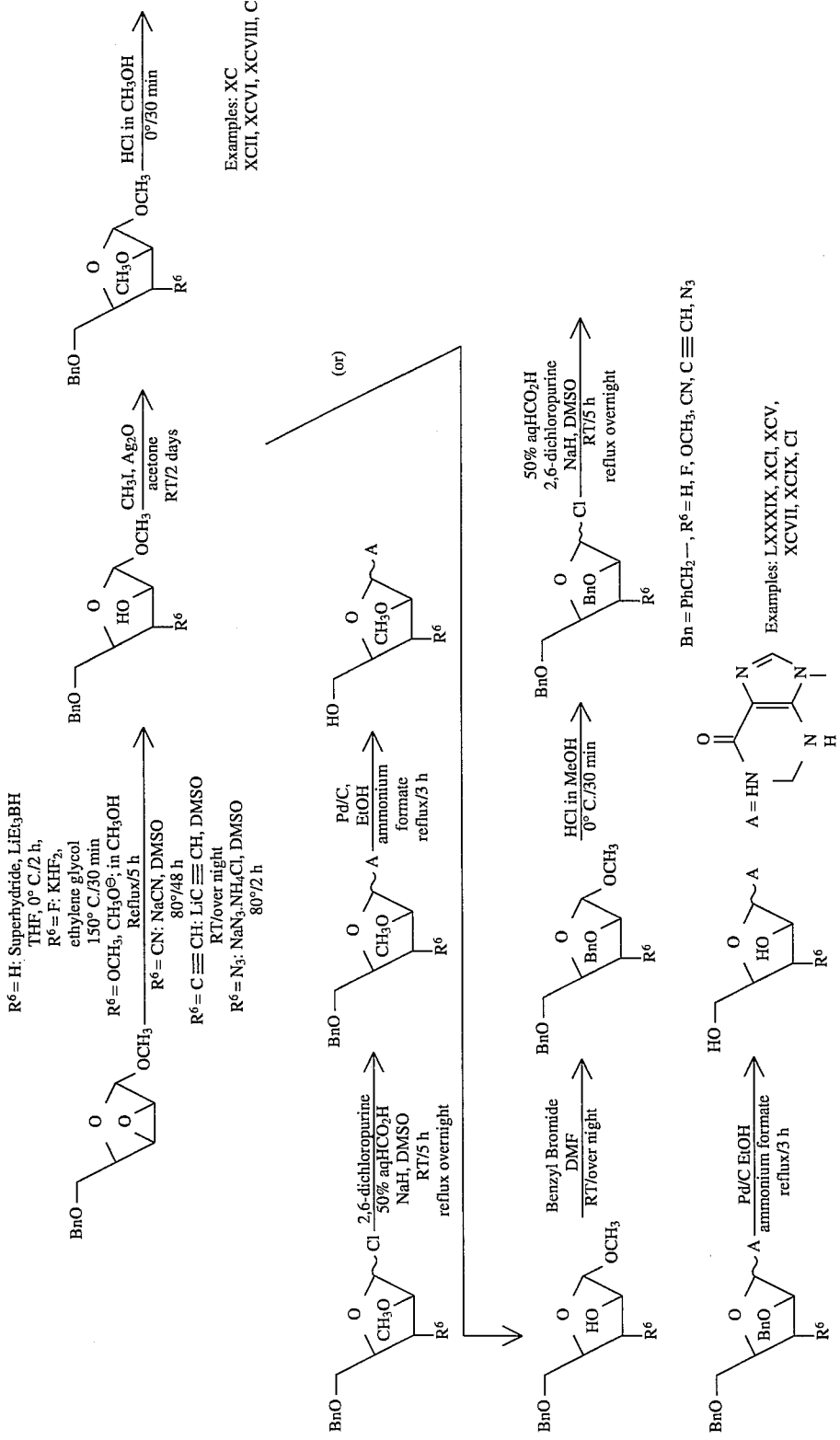

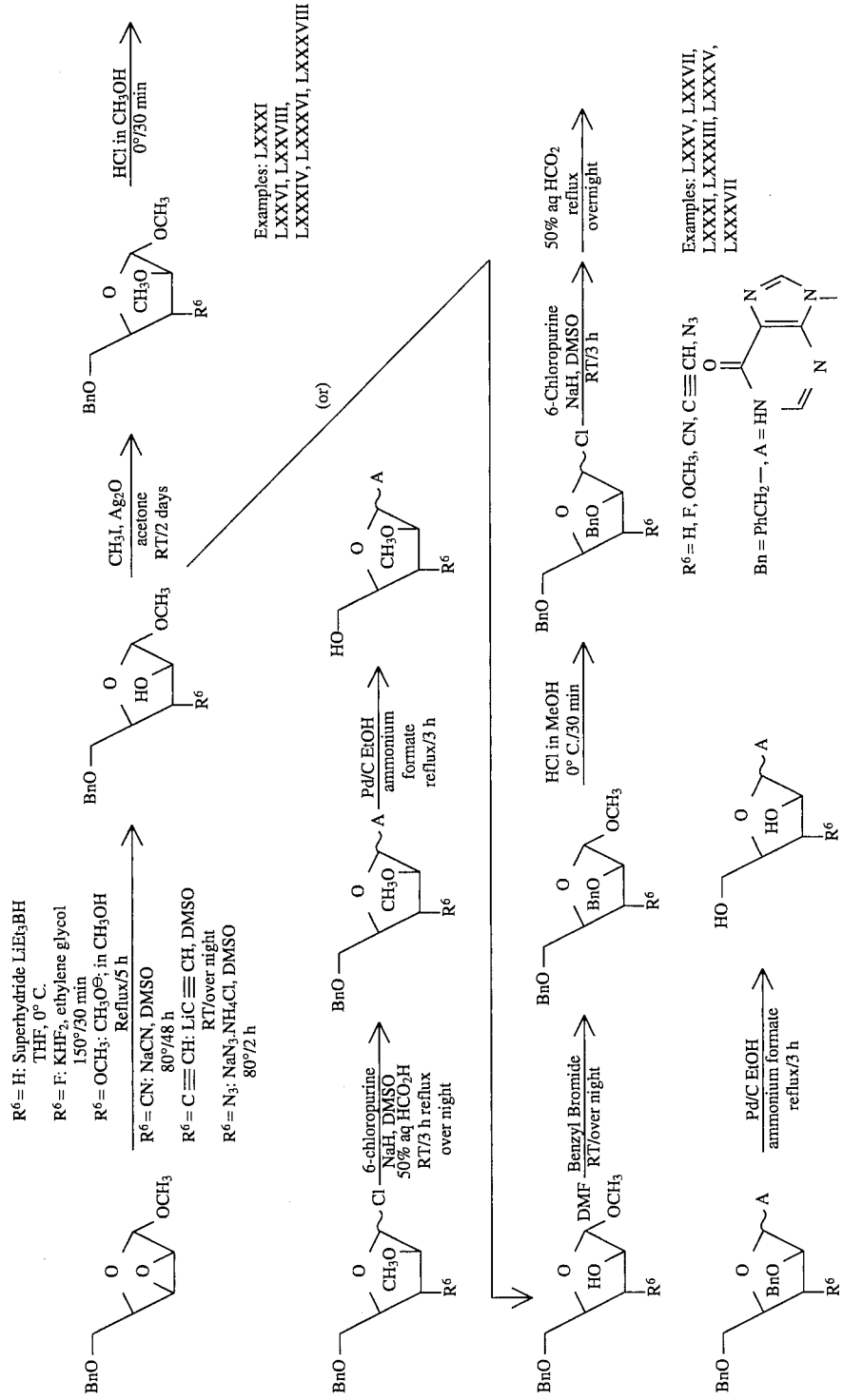

REACTION SCHEME 5

Compounds having the formulas

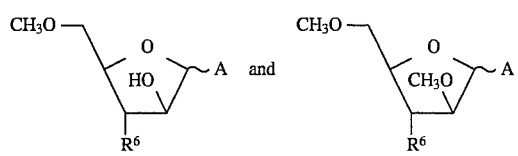

are obtained by using

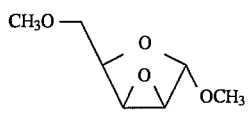

as a starting material and performing exactly the same reactions, and using the same reaction conditions that have been described in reaction scheme 4. Compounds having the formula

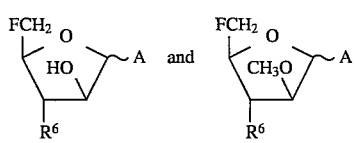

are similarly obtained from the starting material

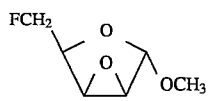

with the use of the same reactions and reactions conditions as described in scheme 4. These starting materials are obtained in the following way

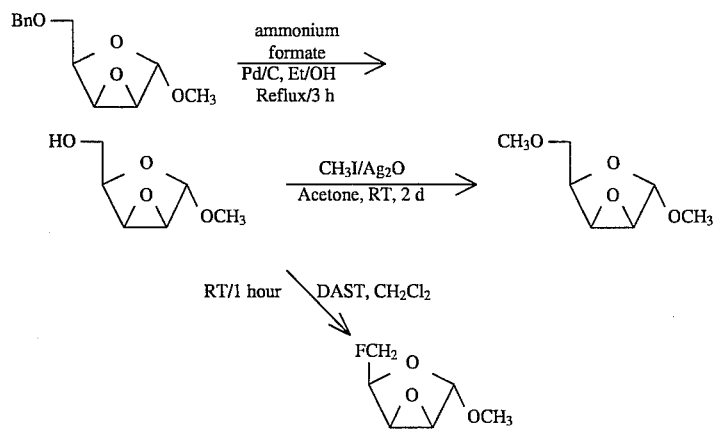

REACTION SCHEME 6

Preparation of compounds XIV–XVI

Compound XVI ($R^1$=OH, $R^2$=Cl, $R^5$=H, $R^6$=F, $R^7$=OH) can be obtained from the compound described in Example I by reacting said compound with N-chlorosuccinimide in methanol

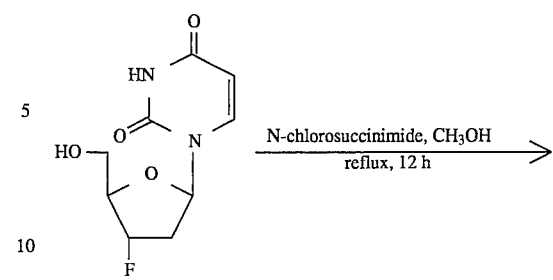

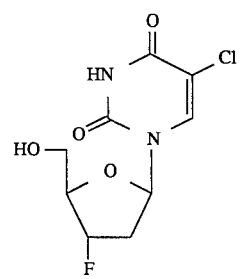

In the same way the compound XIV is prepared by reacting the compound of Example I with N-bromosuccinimide in methanol at room temperature for 12 hours

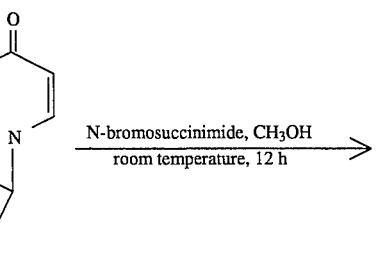

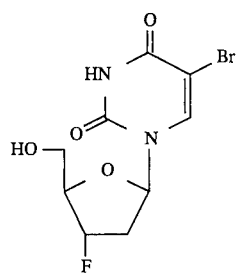

Compound XV (R²=I) is prepared by iodination of the compound of Example I with iodine.

REACTION SCHEME 7

Preparation of compounds XXXVII, XXXVIII, CIII–CXVI

The above compounds are prepared by transglycosidation reactions under the same conditions as described in Example I and II.

The corresponding 2'-deoxy-3'-$R^6$-thymidine derivatives, which are all known compounds and the nucleoside bases of the desired products, are silylated and treated with trimethylsilyl trifluoromethanesulfonate in acetonitrile at room temperature (RT) for 6 days. After separation of the reaction mixture by chromatography the desired products are obtained.

From 3'-methoxythymidine and cytosine, guanine, adenine, hypoxanthine and xanthine, compounds XXXVII, CIII, CVI, CX and CXIV respectively are obtained.

From 3'-acetylene thymidine and the same bases compounds XXXVIII, CV, CVIII, CXII and CXVI respectively are obtained.

From 3'-cyanothymidine and guanine, adenine, hypoxanthine and xanthine, compounds CIV, CVII, CXI and CXV respectively are obtained.

From 3'-fluorothymidine and xanthine and hypoxanthine, compounds CIX and CXIII respectively are obtained.

BIOLOGICAL TESTS

Test I, Effect of Compounds of the Formula I on HIV in H9 Cells

Materials and methods: HIV infection of H9 cells

H9 cells, $10^5$ cells per well on a 24 well plate, suspended in 2 ml RPMI-medium containing 10% fetal calf serum, 100 µg/ml penicillin, 10 µg/ml streptomycin sulfate and 2µg/ml polybrene are exposed to HIV (HTLV-III$_B$) and different concentrations of the test compounds. The plates are incubated at 37° C. in 5% $CO_2$ for 6–7 days. The contents in each well is then homogenized with a pipette and transferred to a centrifuge tube. After centrifugation for 10 min at 1500 rpm the supernatant is removed and the cell pellet is analyzed by fixing in methanol on glass plates. Human HIV positive serum diluted 1:80 or 1:160 is added and incubated for 30 min at 37° C. The plate is then washed with phosphate-buffered saline (PBS) containing $Ca^{2+}$ and $Mg^{2+}$. Sheep antihuman conjugate (FITC) is added and after a new incubation the plate is again washed with PBS. Contrast staining is done with Evans blue and after drying the frequency of HIV antigen containing cells is determined in a microscope. The test result is shown in Table I.

TABLE 1

| Concentration (µM) for 50% Inhibition ($IC_{50}$) of human immuno deficiency virus multiplication in cell culture | |
|---|---|
| Compounds | $IC_{50}$ µM |
| 1-(3'-fluoro-2',3'-dideoxy-β-D-ribofuranosyl)-5-propyluracil (VSA 408) | 1 |
| 1-(3'-fluoro-2',3'-dideoxy-β-D-ribofuranosyl)-5-ethyluracil (VSA 410) | <1 |
| 1-(3'-fluoro-2',3'-dideoxy-β-D-ribofuranosyl)-uracil (VSA 417) | 0.5 |
| 1-(5'-acetyl-3'-fluoro-2',3'-dideoxy-β-D-ribofuranosyl)-5-methyluracil (VSB 423) | <0.01 |

Table I shows that the tested compounds are active inhibitors of HIV virus multiplication.

BIOLOGICAL TEST

The activity against human immunodeficiency virus (HIV) has been tested for the compounds listed and the resulting activities are shown in the Table below.

TABLE 1A

| Inhibition of HIV multiplication in cell culture by some nucleoside analogs. | | | | | |
|---|---|---|---|---|---|
| | | % Inhibition | | | |
| Example | Compound | 10 | 1 | 0.1 | 0.04 µg/ml |
| X | 1-(3'-fluoro-2'-methoxy-2',3'-dideoxy-β-D-arabinofuranosyl)thymine | 85 | 44 | 58 | |
| | | 83 | 11 | | |
| | | 79 | 20 | | |
| XI | 1-(3'-azido-2'-methoxy-2',3'-dideoxy-β-D-arabinofuranosyl)thymine | 73 | 21 | 27 | |
| | | 48 | 38 | 32 | |
| XII | 1-(3'-ethynyl-2',3'-dideoxy)thymidine | 54 | 18 | | |
| XIV | 5-bromo-1-(3'-fluoro-2',3'-dideoxy-β-D-ribofuranosyl)uracil | | | 50 | |
| XV | 5-iodo-1-(3'-fluoro-2',3'-dideoxy-β-D-ribofuranosyl)uracil | | | 50 | |
| XVI | 5-chloro-1-(3'-fluoro-2',3'-dideoxy-β-D-ribofuranoxyluracil | | | | 50 |

The data in the Table were gathered and tests performed as described by Koshida et el., "Inhibition of Human Immunodeficiency Virus in vitro by Combination of 3'-Azido-3'-Deoxythymidine and Foscarnet" in Antimicrob Agents and Chemotherapy, Vol 33 (1989) p. 778–780 (on H9 cells for compounds X–XII) and by De Clercq et el, Nucleosides and Nucleotides, Vol 8 (1989) p. 659–671 (on MT4 cells, literature data for compounds XIV–XVI).

The test values show that all the tested compounds inhibit the multiplication of HIV, at the dose level of 0.1–1 μg/ml.

Test II, Cellular Toxicity

H9 cells, $2\times10^7$ cells per plate, are incubated in RPMI-1540 medium containing 10% fetal calf serum, 70 mg/l penicillin, 100 mg/l streptomycin and 10 mM hepes, in absence or presence of test compounds. The number of cells per plate is determined after 48 h. Cells incubated in the absence of test compounds then underwent two cell division cycles.

F5000 cells, which are human embryo cells, $1\times10^5$ cells per plate, are incubated in Eagle's minimal essential medium, supplemented with Earle's salts, non-essential amino acids, 10% fetal calf serum, 10 mM hopes, 70 mg/l penicillin and 100 mg/l streptomycin, in absence or presence of test compounds. The number of cells per plate is determined after 48 h. Cells incubated in the absence of test compounds underwent one cell division cycle. The results are given as % inhibition of cell multiplication when the concentration of the compound is 100 μM or 250 μM.

TABLE II

Cellular toxicity an Hg and F5000 cells

| Compound | % inhibition (concentration μM) | |
|---|---|---|
| | H9 | F5000 |
| 1-(3'-fluoro-2',3'-dideoxy-β-D-ribofuranosyl)-5-propyluracil (VSA 408) | 15(250) | 0(100) |
| 1-(3'-fluoro-2',3'-dideoxy-β-D-ribofuranosyl)-5-ethyluracil (VSA 410) | 25(100) | 25(100) |
| 1-(3'-fluoro-2',3'-dideoxy-β-D-ribofuranosyl)-uracil (VSA 417) | | 10(100) |

Table II shows that the concentrations at which the compounds exhibit toxicities, vastly exceed the concentrations needed for 50% inhibition of HIV multiplication as given in table I.

We claim:

1. A compound of the formula:

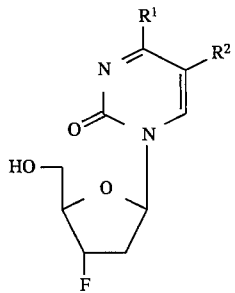

wherein $R^1$ is OH or $NH_2$;

$R^2$ is $CF_3$, $CH_2CH_2CH_3$,

$CH_2OCH_3$, $CH_2SCH_3$, $CH{=}CH_2$ $CH{=}CH{-}CH_3$, $C{\equiv}CH$, $C{\equiv}C{-}CH_3$ or $CH_2{-}C{\equiv}CH$;

or a pharmaceutically acceptable salt thereof.

2. A pharmaceutical composition comprising a compound of formula:

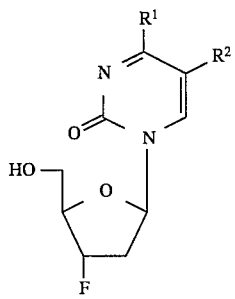

wherein $R^1$ is OH or $NH_2$;

$R^2$ is $CF_3$, $CH_2CH_2CH_3$,

$CH_2OCH_3$, $CH_2SCH_3$, $CH{=}CH_2$ $CH{=}CH{-}CH_3$, $C{\equiv}CH$, $C{\equiv}C{-}CH_3$ or $CH_2{-}C{\equiv}CH$;

or a pharmaceutically acceptable salt thereof; and a pharmaceutically acceptable carrier.

3. The compound according to claim 1 wherein $R^1$ is OH.

4. The composition according to claim 2 wherein $R^1$ is OH.

5. The compound according to claim 1 wherein $R^2$ is $C{\equiv}CH$, $C{\equiv}C{-}CH_3$, or $CH_2{-}C{\equiv}CH_3$.

6. The composition according to claim 2 wherein $R^2$ is $C{\equiv}CH$, $C{\equiv}C{-}CH_3$ or $CH_2{-}C{\equiv}CH_3$.

* * * * *